United States Patent
Gordeev et al.

(12) 
(10) Patent No.: US 6,413,724 B1
(45) Date of Patent: *Jul. 2, 2002

(54) SOLID PHASE AND COMBINATORIAL LIBRARY SYNTHESES OF FUSED 2,4-PYRIMIDINEDIONES

(75) Inventors: Mikhail F. Gordeev, San Leandro; Dinesh V. Patel, Fremont, both of CA (US)

(73) Assignee: Versicor, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/795,189

(22) Filed: Feb. 4, 1997

Related U.S. Application Data

(63) Continuation-in-part of application No. 08/740,103, filed on Oct. 28, 1996, now Pat. No. 6,025,371.

(51) Int. Cl.$^7$ ............... G01N 33/53; G01N 33/543; C07D 239/72

(52) U.S. Cl. ............ 435/7.1; 436/518; 544/285; 544/256; 544/279; 544/258; 435/DIG. 1; 435/DIG. 22; 435/DIG. 34; 435/DIG. 40

(58) Field of Search ............ 436/518; 435/7.1, 435/DIG. 1, DIG. 22, DIG. 34, DIG. 40; 544/285, 256, 279, 258

(56) References Cited

U.S. PATENT DOCUMENTS

| | | |
|---|---|---|
| 4,521,420 A | 6/1985 | Maurer et al. |
| 4,631,211 A | 12/1986 | Houghten |
| 4,835,157 A | 5/1989 | Press et al. |
| 5,463,564 A | 10/1995 | Agrafiotis et al. |
| 5,510,240 A | 4/1996 | Lam et al. |
| 5,549,974 A | 8/1996 | Holmes |

FOREIGN PATENT DOCUMENTS

| | | |
|---|---|---|
| CA | 2053475 | 4/1992 |
| EP | 0481342 | 4/1992 |
| EP | 0 640 606 A1 | 3/1995 |
| WO | WO 86/00991 | 2/1986 |
| WO | WO 96/24597 | 8/1996 |

OTHER PUBLICATIONS

Smith et al., Bioorganic & Medicinal Chemistry Letters., vol. 6., No. 13., pp. 1483–1486., Jun. 1996.*

Gordeev et al., Tetrahedron Letters., vol. 37., No. 27., pp. 4643–4646., 1996.*

Patel et al (Molecular Diversity and Combinatorial Chemistry Libraries and Drug Discovery., Edited by Irwin M. Chaiken, Kim D. Janda., American Chemical Society, Washington, D.C., pp. 58–69., Feb. 1996.*

Gordon et al (Journal of Medicinal Chemistry., vol. 37., No. 10., pp. 1385–1401., May 13, 1994).*

Berge, J. and Moore, G.N., "An alternative route to aryloxymethylphosphonates and phosphinates via fluoride ion displacement from activated aromatic substrates" *SYNLETT* 3:187–188 (1994).

Bush et al., "Kinetic interactions of tazobactam with β–lactamases from all major structural classes" *Antimicrobial Agents and Chemotherapy* 37(4):851–858 (1993).

Cecchetti et al., "4H–1–benzothiopyran–4–one–3–carboxylic acids and 3,4–dehydro–2H–isothiazolo[5,4–b][1]benzothiopyran–3, 4–diones as quinolone antibacterial analogs" *J. Heterocyclic Chem.* 30:1143–1148 (1993).

Cottam et al., "Substitued Xanthines, Pteridinediones, and related compounds as potential antiinflammatory agents. Synthesis and biological evaluation of inhibitors of tumor necrosis factor α" *J. Med. Chem.* 39(1):2–9 (1996)/.

Fuson et al., "Displacement of nuclear halogen atoms in hindered aryl ketones by the action of grignard reagents" *J. Am. Chem. Soc.* 76:5119–5121 (1954).

Gouilleux et al., "Solid phase synthesis of chiral 3–substituted quinazoline–2,4–diones" *Tetrahedron Lett.* 37(39):7031–7034 (1996).

Inoue et al., "Synthesis and antibacterial activity of thiazolopyrazine–incorporated tetracyclic quinolone antibacterials" *J. Med. Chem.* 37:586–592 (1994).

Ishii et al., "Highly selective aldose reductase inhibitors. 1. 3–(Arylalkyl)–2,4,5–trioxoimidazolidine–1–acetic acids" *J. Med. Chem.* 39:1924–1927 (1996).

Kalindjian, S.B. and Smith, R.A.G., "Preparation of tert-butyl 4–N–(ω–aminoalkyl)aminobenzoates by nucleophilic aromatic substitution" *SYNLETT* 11:803–804 (1991).

Lorian, V., in: Antibiotics in Laboratory Medicine, Fourth Edition, Williams & Wilkins, Baltimore, MD, pp. 546–551 (1996).

Luo, Y. and Potvin, P.G., "Chelation–controlled regioselectivity in the synthesis of substituted pyrazolylpyridine ligands" *J. Org. Chem.* 59:1761–1765 (1994).

Malamas, M.S. and Millen, J., "Quinazolineacetic acids and related analogues as aldose reductase inhibitors" *J. Med. Chem.* 34:1492–1503 (1991).

Ogawa et al., "Preparation of thienopyrimidinediones as aldose reductase inhibitors" *Chem. Abstracts* 114:756 Abstract No. 102035e (1991).

Reisch et al., "Alkylation of quinazoline–2,4(1H,3H)–diones with 1,4–dibromo–2–methylbut–2–ene under phase-–transfer–catalysis" *J. Heterocyclic Chem.* 30:1117–1120 (1993).

(List continued on next page.)

*Primary Examiner*—Padmashri Ponnaluri
(74) *Attorney, Agent, or Firm*—Morrison & Foerster LLP

(57) ABSTRACT

The invention provides chemistry libraries containing fused 2,4-pyrimidinediones. The invention also provides methods for the construction of fused 2,4-pyrimidinedione containing libraries. The invention further provides methods for the identification of bioactive, fused 2,4-pyrimidinediones from those libraries.

5 Claims, 7 Drawing Sheets

OTHER PUBLICATIONS

Stabler, S.R. and Jahangir, "Preparation of N–arylated heterocycles by nucleophilic aromatic substitution" *Synthetic Comm.* 24:(1):123–129 (1994).

Yeager, G.W. and Schissel, D.N., "A convenient method for the preparation of 4–aryloxyphenols" *Synthesis* 1:63–68 (1991).

Ziegler, Jr. et al., "Synthesis of some novel 7–substituted quinolonecarboxylic acids via nitroso and nitrone cycloadditions" *J. Heterocyclic Chem.* 25(3):719–723 (1988).

Ziegler Jr. et al., "Synthesis and In Vitro biological activity of some 7–[hydrazino],–[hydrazonyl] and –[pyrazolyl] quinolone–3–carboxylic acids" *J. Heterocyclic Chem.* 25(5):1543–1546 (1988).

Buckman et al., "Solid–phase synthesis of 1,3–dialkyl quinazoline–2,4–diones" *Tetrahedron Lett.* (1996) 37:4439–4442.

Bunin et al., "A general and expedient method for the solid–phase synthesis of 1,4–benzodiazepine derivatives" *J. Am. Chem. Soc.* (1992) 114:10997–10998.

Canonne et al., "Synthesis of chiral 3–substituted 2,4(1H, 3H)–quinazolinediones" *Heterocycles* (1993) 36:1305–1314.

Cho et al., "An unnatural biopolymer" *Science* (1993) 261:1303–1305.

Evans et al., "The asymmetric synthesis of α–amino acids. Electrophilic azidation of chiral imide enolates, a practical approach to the synthesis of (R)– and (S)–α–azido carboxylic acids" *J. Amer. Chem. Soc.* (1990) 112:4011–4030.

Furka et al., "General method for rapid synthesis of multicomponent peptide mixtures" *Int. J. Peptide Protein Res.* (1991) 37:487–493.

Fodor et al., "Light–directed, spatially addressable parallel chemical synthesis" *Science* (1991) 251:767–773.

Geysen et al., "Use of peptide synthesis to probe viral antigens for epitopes to a resolution of a single amino acid" *Proc. Natl. Acad. Sci. USA* (1984) 81:3998–4002.

Gordon et al., "Strategy and tactics in combinatorial organic synthesis. Applications to drug discovery" *Acc. Chem. Res.* (1995) 29:144–154.

Gordon et al., "Reductive alkylation on a solid phase: Synthesis of a piperazinedione combinatorial library" *Biorg. Medicinal Chem. Lett.* (1995) 5:47–50.

Grant, G.A., ed., *Synthetic Peptides. A User's Guide* (1992) W.H. Freeman and Co., New York. A title page and table of contents are enclosed herewith.

Greene et al., *Protective Groups in Organic Synthesis,* 2d Ed., (1991) John Wiley & Sons, Inc., New York. A title page and table of contents are enclosed herewith.

Harper et al., *Review of Physiological Chemistry,* 16th Ed., (1977) Lange Medical Publications, pp. 21–24.

Hermkens et al., "Solid–phase organic reactions: A review of the recent literature" *Tetrahedron* (1996) 52:4527–4554.

Houghten, "General method for the rapid solid–phase synthesis of large numbers of peptides: Specificity of antigen–antibody interaction at the level of individual amino acids" *Proc. Natl. Acad. Sci. USA* (1985) 82:5131–5135.

Houghten et al., "Generation and use of synthetic peptide combinatorial libraries for basic research and drug discovery" *Nature* (1991) 354:84–86.

Hutchins et al., "A general method for the solid phase synthesis of ureas" *Tetrahedron Lett.* (1994) 35:4055–4058.

Lam et al., "A new type of synthetic peptide library for identifying ligand–binding activity" *Nature* (1991) 354:82–84.

Lowe, III et al., "Structure–activity relationship of quinazolinedione inhibitors of calcium–independent phosphodiesterase" *J. Med. Chem.* (1991) 34:624–628.

Maillard et al., "Dérivés de la (3H) quinazolinone–4 doués de propriétés anti–inflammatoires. III. Dérivés de la 1H–3H–quinazoline–dione–2,4 et produits voisins"*Fr. Chim. Ther.* (1968) 3:100–105.

Merrifield, "Solid phase peptide synthesis. I. The synthesis of a tetrapeptide" *J. Am. Chem. Soc.* (1963) 85:2149–2154.

Mignani et al., "New indole derivatives as potent and selective serotonin uptake inhibitors" *Bioorg. Med. Chem. Lett.* (1993) 3:1913–1918.

Montginoul et al., "Activités analgésiques, anticonvulsivantes et anti–inflammatoires de 1H, 3H–quinazolinediones–2,4" *Ann. Pharm. Franc.* (1988) 46:223–232.

Murphy et al., "Combinatorial organic synthesis of highly functionalized pyrrolidines: Identification of a potent angiotensin converting enzyme inhibitor from a mercaptoacyl proline library" *J. Am. Chem. Soc.* (1995) 117:7029–7030.

Rich et al., "Preparation of a new o–nitrobenzyl resin for solid–phase synthesis of tert–butyloxycarbonyl–protected peptide acids" *J. Am. Chem. Soc.* (1975) 97:1575–1579.

Roth et al., *Pharmaceutical Chemistry, Volume 1: Drug Synthesis* (1988) John Wiley & Sons, Inc., New York, pp. 326–329.

Simon et al., "Peptoids: A modular approach to drug discovery" *Proc. Natl. Acad. Sci. USA* (1992) 89:9367–9371.

Wang et al., "Solid phase synthesis of protected peptides via photolytic cleavage of the α–methylphenacyl ester anchoring linkage" *J. Org. Chem.* (1976) 41:3258–3261.

Williams, *Synthesis of Optically Active α–Amino Acids,* (1989) Pergamon Press. A title page and table of contents are enclosed herewith.

Williams et al., "Asymmetric synthesis of monosubstituted and α,α–disubstituted α–amino acids via diastereoselective glycine enolate alkylations" *J. Amer. Chem. Soc.* (1991) 113:9276–9286.

\* cited by examiner

2,4-Quinazolinediones

Pyrimidopyrimidinediones

Pyridopyrimidinediones

2,4-Pteridinediones    Pyrimidopyridazinediones

Azolopyrimidinediones

X=O, S, NR$_5$ $R_2$ can represent from 1 to 3 (different) substituent(s)

SOLID PHASE AND COMBINATORIAL LIBRARY SYNTHESES OF FUSED 2,4-PYRIMIDINEDIONES

This application is a continuation-in-part of application Ser. No. 08/740,103, filed Oct. 28, 1996, now U.S. Pat No. 6,025,371.

TECHNICAL FIELD

This invention is directed to combinatorial chemistry libraries containing fused 2,4-pyrimidinediones. This invention is further directed to methods for constructing combinatorial chemistry libraries containing fused 2,4-pyrimidinediones. This invention is still further directed to methods for the identification of bioactive fused 2,4-pyrimidinediones.

BACKGROUND ART

Modem day drug discovery is a multi-faceted endeavor. Researchers commonly delineate a biochemical pathway that is operative in a targeted pathological process. This pathway is analyzed with an eye toward determining its crucial elements: those enzymes or receptors that, if modulated, could inhibit the pathological process. An assay is constructed such that the ability of the important enzyme or receptor to function can be measured. The assay is then performed in the presence of a variety of molecules. If one of the assayed molecules modulates the enzyme or receptor in a desirable fashion, this molecule may be used directly in a pharmaceutical preparation or can be chemically modified in an attempt to augment its beneficial activity. The modified molecule that exhibits the best profile of beneficial activity may ultimately be formulated as a drug for the treatment of the targeted pathological process.

With the use of high-throughput screening techniques, one can assay the activity of tens of thousands of molecules per week. Where molecules can only be synthesized one at a time, the rate of molecule submission to an assay becomes a debilitating, limiting factor. This problem has led researchers to develop methods by which large numbers of molecules possessing diverse chemical structures can be rapidly and efficiently synthesized. One such method is the construction of chemical combinatorial libraries.

Chemical combinatorial libraries are diverse collections of molecular compounds. Gordon et al. (1995) *Acc. Chem. Res.* 29:144–154. These compounds are formed using a multistep synthetic route, wherein a series of different chemical modules can be inserted at any particular step in the route. By performing the synthetic route multiple times in parallel, each possible permutation of the chemical modules can be constructed. The result is the rapid synthesis of hundreds, thousands, or even millions of different structures within a chemical class.

For several reasons the initial work in combinatorial library construction focused on peptide synthesis. Furka et al. (1991) *Int. J. Peptide Protein Res.* 37:487–493; Houghton et al. (1985) *Proc. Natl. Acad. Sci. USA* 82:5131–5135; Geysen et al. (1984) *Proc. Natl. Acad. Sci. USA* 81:3998–4002; and Fodor et al. (1991) *Science* 25:767. The rapid synthesis of discrete chemical entities is enhanced where the need to purify synthetic intermediates is minimized or eliminated; synthesis on a solid support serves this function. Construction of peptides on a solid support is well-known and well-documented. Obtaining a large number of structurally diverse molecules through combinatorial synthesis is furthered where many different chemical modules are readily available; hundreds of amino acid modules are commercially available. Finally, many peptides are biologically active, making them interesting as a class to the pharmaceutical industry.

The scope of combinatorial chemistry libraries has recently been expanded beyond peptide synthesis. Polycarbamate and N-substituted glycine libraries have been synthesized in an attempt to produce libraries containing chemical entities that are similar to peptides in structure, but possess enhanced proteolytic stability, absorption and pharmacokinetic properties. Cho et al. (1993) *Science* 261:1303–1305; Simon et al. (1992) *Proc. Natl. Acad. Sci. USA* 89:9367–9371. Furthermore, benzodiazepine, pyrrolidine, and diketopiperazine libraries have been synthesized, expanding combinatorial chemistry to include heterocyclic entities. Bunin et al. (1992) *J. Am. Chem. Soc.* 114:10997–10998; Murphy et al. (1995) *J. Am. Chem. Soc.* 117:7029–7030; and Gordon et al. (1995) *Biorg. Medicinal Chem. Lett.* 5:47–50.

Pyrimidinediones are a class of bioactive, heterocyclic molecules that have attracted considerable attention in the pharmaceutical industry. The benzo derivatives of this series (2,4-quinazolinediones) are represented as anti-inflammatory agents, analgesics, anticonvulsants, CNS agents, serotonin uptake inhibitors, antihypertensive agents, cardiovascular agents, and fungicides. Maillard et al. (1968) *Fr. Chim. Ther.* 3:100–106; Montginoul et al. (1988) *Ann. Pharm. Franc.* 46:223–232; Lowe et al. (1991) *J. Med. Chem.* 34:624–628; Mignani et al. (1993) *Bioorg. Med. Chem. Lett.* 3:1913–1918; Can. Pat. Appl. CA 2053475; Eur. Pat. Appl. EP 481342; and Smith et al. (1996) *Bioorg. Med. Chem. Lett.* 6:1483–1486. Naturally occurring bioactive compounds, such as theophylline and theobromine, that have found application as cardiotonic agents, broncholytic agents, vasodilators, psychotonic agents, and circulation analeptic agents are heterocyclic ring fused 2–4-pyrimidinediones. Roth et al. In: *Pharmaceutical Chemistry. Volume* 1: *Drug Synthesis* (1988) John Wiley & Sons. Recently, synthetic heterocyclic fused 2,4-pyrimidinediones, such as thieno and furopyrimidine-2,4-diones have been patented as serotonin antagonists and alpha adrenergic blocking agents. U.S. Pat. No. 4,835,157.

Methods for the solution phase preparation of fused 2,4-pyrimidinediones have been reported. For example, the solution phase synthesis of pyridopyrimidinediones and quinazolinediones by the reaction, respectively, of an aminonicotinic ester or anthranilate derivative with isocyanate has been described. Lowe et al. (1991) *J. Med. Chem.* 34:624–628. The reaction of a carbomethoxyphenyl isocyanate with an amino acid is a further described example of solution phase chemistry used to construct fused pyrimidinediones. Canonne et al. (1993) *Heterocycles* 36:1305–1314. Little work, however, has been reported on the solid phase synthesis of fused 2,4-pyrimidinediones.

An 11 step synthesis of particularly substituted 2,4-quinazolinediones using solid phase synthesis that proceeds through an anthranilate intermediate has been described. Buckman et al. (1996) *Tetrahedron Lett.* 37:4439–4442. This synthetic route is inherently limited, however, to the production of phenolic 2,4-quinazolinediones due to the mode of connection between the 2,4-quinazolinedione and the solid support. Furthermore, the synthetic route is limited by the harshness of the reaction conditions employed. For instance, the cyclization of the pyrimidinedione ring requires the presence of strong potassium hydroxide: a reagent that could cause cleavage of the compound from the solid support, destroy certain functional groups such as esters, or racemize chiral groups such as amino acid derivatives. Finally, the synthetic route requires the use of air-sensitive reagents, such as lithium benzyloxazolidinone, making the automation of the synthetic protocol difficult, thus potentially reducing its application to the manual synthesis of a limited number of 2,4-quinazolinediones.

A 5 step synthesis of 2,4-quinazolinediones using solid phase synthesis that proceeds through an anthranilate intermediate has been described. Smith et al. (1996) *Biorg. & Medicinal Chem. Lett.* 6:1483–1486. This route is limited in that it does not allow for the production of 2,4-quinazolinediones bound to a solid support: the last step of the synthesis both completes the pyrimidinedione ring and releases the formed compound from the solid support. The route is further limited in that it employs a moisture-sensitive chloroformate derivatized polymeric support that has to be prepared immediately before use. Finally, the final synthetic step requires a high reaction temperature virtually excluding the application of standard equipment used for the automated synthesis of combinatorial libraries. Therefore the scope of the application of this method is severely limited.

A four step synthesis of pyrido[2,3-d]pyrimidines has been described. Gordeev et al. (1996) *Tetrahedron Lett.* 37:4643–4646. This route is limited to the production of particularly substituted pyridopyrimidines. Due to the nature of the linkage between the pyridopyrimidine and the solid support, only those compounds with a carboxyl group in the 6-position can be accessed.

Methods for nucleophilic aromatic substitution reactions have been described, where a fluoride substituent on an aromatic ring is displaced from a chemical intermediate that is attached to a solid support. MacDonald et al. discloses the use of a nucleophilic aromatic substitution reaction on a solid support as a step in the preparation of a quinolone library. (1996) *Tetrahedron Lett.* 37: 4815–4818. Phillips et al. describes the use of a nucleophilic aromatic substitution reaction in the solid phase preparation of benzimidazoles. (1996) *Tetrahedron Lett.* 37: 4887–4890. Shapiro et al. delineates the use of $^{19}$F NMR monitoring of a nucleophilic aromatic substitution reaction on a solid support. (1996) *Tetrahedron Lett.* 37: 4671–4674. None of these references either disclose or suggest the use of a nucleophilic aromatic substitution reaction in the preparation of a fused 2,4-pyrimidinedione library on a solid support.

The cited references in the background section, and in the following sections, are herein incorporated by reference.

DISCLOSURE OF THE INVENTION

The present invention provides a combinatorial library that contains a fused 2,4-pyrimidinedione (shown below, I):

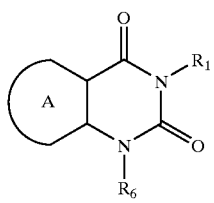

I where the 'A' ring is an aromatic ring, a heteroaromatic ring, an aliphatic ring or substituted versions thereof.

In one embodiment, the combinatorial library contains fused 2,4-pyrimidinediones selected from the group: 2,4-quinazolinediones, pyrimidopyrimidinediones, pyridopyrimidinediones, 2,4-pteridinediones, and azolopyrimidinediones (FIG. 1, where $R_2$–$R_6$ can independently be alkyl, aryl, heteroaryl, electron withdrawing groups, and amino acid derivatives). Preferably, the combinatorial library contains fused 2,4-pyrimidinediones including but not limited to: 2,4-quinazolinediones, pyrimidopyrimidinediones, and azolopyrimidinediones.

In another embodiment, the combinatorial library contains fused 2,4-pyrimidinediones, where $R_1$ in the fused 2,4-pyrimidinedione is:

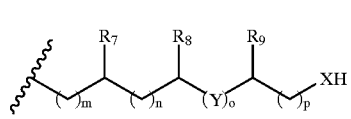

II where $R_7$, $R_8$, and $R_9$ are independently selected from the group H, alkyl, aryl, OH, $NH_2$, $NHR_{10}$, $NR_{10}R_{11}$, SH, $SR_{10}$, =O, $C(O)R_{10}$, and an amino acid side chain; and where Y is selected from the group alkyl, aryl, O, NH, and $NR_{10}$; and where XH is selected from the group $CO_2H$, $CO_2R_{10}$, $C(O)R_{10}$, SH, OH, $NH_2$, $NHR_{10}$, $C(O)NHOH$, and $C(O)NHR_{10}$; and further where m, n, o, and p vary independently from 0 to 4, and where $R_{10}$ and $R_{11}$ are independently selected from the group alkyl, aryl and heteroaryl.

In another embodiment, the combinatorial library contains fused 2,4-pyrimidinediones, where $R^1$ in the fused 2,4-pyrimidinedione is:

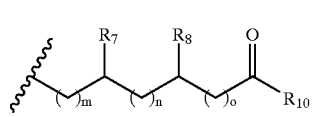

III where $R_7$ and $R_8$ are independently selected from the group H, alkyl, aryl, OH, $NH_2$, $NHR_{10}$, $NR_{10}R_{11}$, SH, $SR_{10}$, =O, $C(O)R_{10}$, and an amino acid side chain; and where m, n, and o vary independently from 0 to 4; and where $R_{10}$ and $R_{11}$ are independently selected from the group alkyl, aryl and heteroaryl.

In another embodiment, the combinatorial library contains fused 2,4-pyrimidinediones, where $R^1$ in the fused 2,4-pyrimidinedione is:

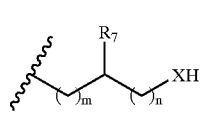

IV where $R_7$ is independently selected from the group H, alkyl, aryl, OH, $NH_2$, $NHR_{10}$, $NR_{10}R_{11}$, SH, $C(O)R_{10}$, and an amino acid side chain; and where XH is selected from the group $CO_2H$, $CO_2R_{10}$, $C(O)R_{10}$, SH, OH, $NH_2$, $NHR_{10}$, $C(O)NHOH$, and $C(O)NHR_{10}$; and where m, and n vary independently from 0 to 4; and where $R_{10}$ and $R_{11}$ are independently selected from the group alkyl, aryl and heteroaryl.

The present invention also provides a combinatorial library that contains fused 2,4-pyrimidinediones, where the fused 2,4-pyrimidinediones are connected to a solid support via $R_1$, and where the fused 2,4-pyrimidinedione is selected from the group: 2,4-pteridinediones, pyridopyrimidinediones, pyrimidopyridazinediones and azolopyrimidinediones.

In one embodiment, the combinatorial library contains fused 2,4-pyrimidinediones selected from the group: 2,4- pteridinediones, pyridopyrimidinediones, and pyrimidopyridazinediones.

In another embodiment, the combinatorial library contains pyridopyrimidines.

The present invention also provides a combinatorial library that contains fused 2,4-pyrimidinediones, where the fused 2,4-pyrimidinediones are connected to a solid support through a substituent at the 3-position.

In another embodiment, the combinatorial library contains fused 2,4-pyrimidinediones selected from the group: 2,4-quinazolinediones, pyrimidopyrimidinediones, pyridopyrimidinediones, 2,4-pteridinediones, and azolopyrimidinediones.

In another embodiment, the combinatorial library contains fused 2,4-pyrimidinediones selected for the group: 2,4-quinazolinediones, pyrimidopyrimidinediones, and pyridopyrimidinediones.

In another embodiment, the combinatorial library contains a 2,4-quinazolinedione.

The present invention also provides a combinatorial library that contains fused 2,4-pyrimidinediones that is prepared by cleaving the fused 2,4-pyrimidinediones from a solid support.

The present invention also provides a combinatorial library that contains fused 2,4-pyrimidinediones that possess a substituent at the 3-position, where the library is prepared by cleaving the fused 2,4-pyrimidinedione from a solid support.

In one embodiment, this method includes a step where a fluoride substituent is displaced in a nucleophilic aromatic substitution reaction.

The present invention also provides a method of producing a combinatorial library that contains fused 2,4-pyrimidinediones, where the fused 2,4-pyrimidinediones are connected to a solid support, and where the fused 2,4-pyrimidinedione is selected from the group: 2,4-pteridinediones, pyridopyrimidinediones, pyrimidopyridazinediones and azolopyrimidinediones.

In one embodiment, this method includes a step where a fluoride substituent is displaced in a nucleophilic aromatic substitution reaction.

The present invention also provides a method of producing a combinatorial library that contains fused 2,4-pyrimidinediones, where the fused 2,4-pyrimidinediones are connected to a solid support through a substituent at the 3-position.

In one embodiment, this method includes a step where a fluoride substituent is displaced in a nucleophilic aromatic substitution reaction.

The present invention also provides a method of screening a library that contains a fused 2,4-pyrimidinedione.

In one embodiment, the fused 2,4-pyrimidinediones that are screened are connected to a solid support.

In another embodiment, the fused 2,4-pyrimidinediones that are screened are in solution.

BEST MODE FOR CARRYING OUT THE INVENTION

Definitions

Figure 1:
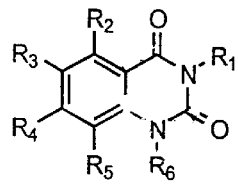
FIG. 1 illustrates the general chemical structures of 2,4-quinazolinediones, pyrimidopyrimidinediones, pyridopyrimidinediones, 2,4-pteridinediones, and azolopyrimidinediones.
Figure 1:
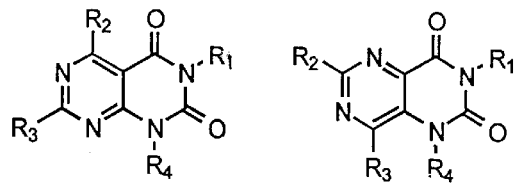
Figure 1:
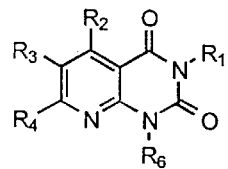
Figure 1:
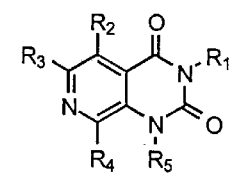
Figure 1:
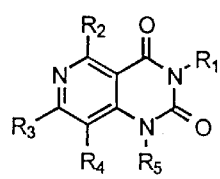
Figure 1:
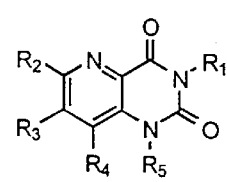
Figure 1:
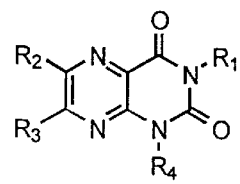
Figure 1:
Figure 1:
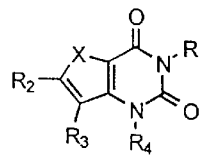
Figure 1:
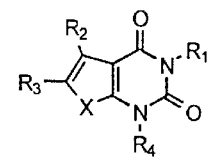
Figure 1:
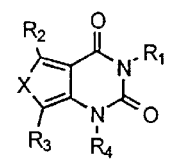
Figure 1:
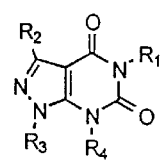
Figure 1:
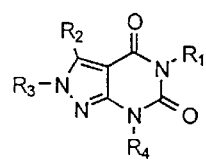

"Bioactive" molecule refers to a molecule that exhibits a dissociation constant of $10^{-6}$ or less when combined with a targeted cellular ligand, including but not limited to, enzymes and receptors.

"Chemical library" or "array" is an intentionally created collection of differing molecules which can be prepared synthetically and screened for biological activity in a variety of different formats (e.g., libraries of soluble molecules, libraries of molecules bound to a solid support).

"Alkyl" refers to a cyclic, branched, or straight chain chemical group containing only carbon and hydrogen, such as methyl, pentyl, and adamantyl. Alkyl groups can either be unsubstituted or substituted with one or more substituents, e.g., halogen, alkoxy, acyloxy, amino, hydroxyl, mercapto, carboxy, benzyloxy, phenyl, benzyl, or other functionality that may be suitably blocked, if necessary for purposes of the invention, with a protecting group. Alkyl groups can be saturated or unsaturated (e.g., containing $-C=C-$ or $-C\equiv C-$ subunits), at one or several positions. Typically, alkyl groups will comprise 1 to 12 carbon atoms, preferably 1 to 10, and more preferably 1 to 8 carbon atoms.

"Amino acid" refers to any of the naturally occurring amino acids, as well as optical isomers (enantiomers and diastereomers), synthetic analogs and derivatives thereof. α-Amino acids comprise a carbon atom to which is bonded an amino group, a carboxyl group, a hydrogen atom, and a distinctive group referred to as a "side chain". The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine and tryptophan), substituted arylalkyl (e.g., as in tyrosine), and heteroarylalkyl (e.g., as in histidine). See, e.g., Harper et al. (1977) *Review of Physiological Chemistry*, 16th Ed., Lange Medical Publications, pp. 21–24. One of skill in the art will appreciate that the term "amino acid" also includes β- γ-, δ-, and ω-amino acids, and the like. Unnatural amino acids are also known in the art, as set forth in, for example, Williams (ed.), Synthesis of Optically Active α-Amino Acids, Pergamon Press (1989); Evans et al., *J. Amer. Chem. Soc.*, 112:4011–4030 (1990); Pu et al., *J. Amer. Chem. Soc.*, 56:1280–1283 (1991); Williams et al., *J. Amer. Chem. Soc.*, 113:9276–9286 (1991); and all references cited therein.

"Aryl" or "Ar" refers to a monovalent unsaturated aromatic carbocyclic group having a single-ring (e.g., phenyl)

or multiple condensed rings (e.g., naphthyl or anthryl), which can be optionally unsubstituted or substituted with amino, hydroxyl, lower alkyl, alkoxy, chloro, halo, mercapto, and other substituents.

"Electron withdrawing group" refers to a substituent that draws electrons to itself more than a hydrogen atom would if it occupied the same position in a molecule. Examples of electron withdrawing groups include —$NR_2$, —COOH, —OR, —$SR_2$, —F, —COR, —Cl, —SH, $NO_2$, —Br, —SR, —$SO_2R$, —I, —OH, —CN, —C=CR, —COOR, —Ar, —CH=$CR_2$, where R is akyl, aryl, arylalkyl, or heteroaryl.

"Heteroaryl" or "HetAr" refers to a monovalent unsaturated aromatic carbocyclic group having a single ring (e.g., pryridyl or furyl) or multiple condensed rings (e.g., indolizinyl or benzothienyl) and having at least one hetero atom, such as N, O, or S, within the ring, which can optionally be unsubstituted or substituted with amino, hydroxyl, alkyl, alkoxy, halo, mercapto, and other substituents.

The "3-position" of a fused 2,4-pyrimidinedione is the nitrogen between the two carbonyl groups; the "1-position" of a fused 2,4-pyrimidinedione is the nitrogen attached to the fused ring (as shown below):

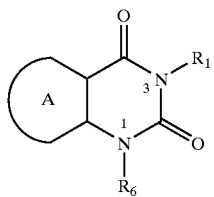

V

"Protecting group" refers to a chemical group that exhibits the following characteristics: (1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) generated in such protected reactions. Examples of protecting groups can be found in Greene et al. (1991) *Protective Groups in Organic Synthesis,* 2nd Ed. (John Wiley & Sons, Inc., New York).

Fused 2,4-Pyrimidinedione Libraries

The present invention provides a combinatorial library containing 2,4-pyrimidinediones that are fused to an aliphatic, an aromatic ring, or a heteroaromatic ring. Fused 2,4-pyrimidinediones are compounds of the following general structure:

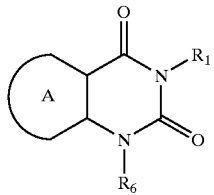

I

Examples of aromatic and heteroaromatic fused 2,4-pyrimidinediones include, but are not limited to, 2,4-quinazolinediones, pyrimidinediones, pyridopyrimidinediones, 2,4-pteridinediones, pyrimidopyridazinediones, and azolopyrimidinediones (shown in FIG. 1). $R_2$, $R_3$, $R_4$, $R_5$, and $R_6$ in FIG. 1 can independently be an alkyl group, an aryl group, a heteroaryl group, and an electron withdrawing group.

When the fused 2,4-pyrimidinedione is not attached to a solid support, $R^1$ can be a substituted alkyl group represented by one of the following three structures:

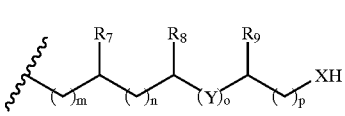

II where $R_7$, $R_8$, and $R_9$ are independently selected from the group H, alkyl, aryl, OH, $NH_2$, $NHR_{10}$, $NR_{10}R_{11}$, SH, $SR_{10}$, =O, $C(O)R_{10}$, and an amino acid side chain; and where Y is selected from the group alkyl, aryl, O, NH, and $NR_{10}$; and where XH is selected from the group $CO_2H$, $CO_2R_{10}$, $C(O)R_{10}$, SH, OH, $NH_2$, $NHR_{10}$, C(O)NHOH, and C(O)$NHR_{10}$; and further where m, n, o, and p vary independently for 0 to 4; and where $R^{10}$ and $R^{11}$ are independently selected from alkyl, aryl, and heteroaryl; or

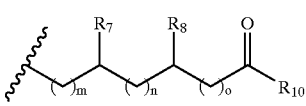

III where $R_7$ and $R_8$ are independently selected from the group H, alkyl, aryl, OH, $NH_2$, $NHR_{10}$, $NR_{10}R_{11}$, SH, $SR_{10}$, =O, $C(O)R_{11}$, and an amino acid side chain; and where m, n, and o vary independently from 0 to 4; and where $R_{10}$ and $R_{11}$ are independently selected from alkyl, aryl, and heteroaryl ; or,

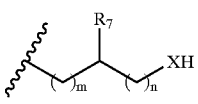

IV where $R_7$ is independently selected from the group H, alkyl, aryl, OH, $NH_2$, $NHR_{10}$, $NR_{10}R_{11}$, SH, =O, $C(O)R_{11}$, and an amino acid side chain; and where XH is selected from the group $CO_2H$, $CO_2R_{10}$, $C(O)R_{10}$, SH, OH, $NH_2$, $NHR_{10}$, C(O)NHOH, and C(O)$NHR_{10}$; and where m and n vary independently from 0 to 4; and where $R_{10}$ and $R_{11}$ are independently selected from alkyl, aryl, and heteroaryl.

When the 2,4-pyrimidinedione library is attached to a solid support, $R_1$ can be a substituted alkyl group represented by one of the following three structures, where the solid support is represented by a darkened circle:

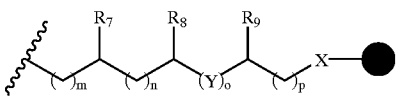

V where $R_7$, $R_8$, and $R_9$ are independently selected from the group H, alkyl, aryl, OH, $NH_2$, $NHR_{10}$, $NR_{10}R_{11}$, SH, $SR_{10}$, =O, $C(O)R_{11}$, and an amino acid side chain; and where Y is selected from the group alkyl, aryl, O, NH, and $NR_{10}$; and where X is selected from the group $CO_2$, CO, S, O, NH, $NR_{10}$, C(O)NHO, and C(O)$NR_{10}$; and further where m, n, o, and p vary independently for 0 to 4; and where $R_{10}$ and $R_{11}$ are independently selected from alkyl, aryl, and heteroaryl; or,

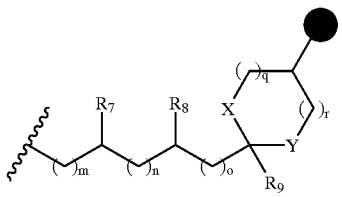

VI where $R_7$, $R_8$, and $R_9$ are independently selected from the group H, alkyl, aryl, OH, $NH_2$, $NHR_{10}$, $NR_{10}R_{11}$, SH, =O, $C(O)R_{11}$, and an amino acid side chain; and where X and Y are independently selected from the group O and S; and where m, n, and o vary independently from 0 to 4 and q and r vary independently from 0 to 2; and where $R_{10}$ and $R_{11}$ are independently selected from alkyl, aryl, and heteroaryl; or,

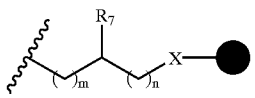

VII where $R_7$ is independently selected from the group H, alkyl, aryl, OH, $NH_2$, $NHR_{10}$, $NR_{10}R_{11}$, SH, $SR_{10}$, =O, $C(O)R_{11}$, and a natural amino acid side chain; and where X is selected from the group $CO_2$, CO, S, O, NH, $NR_{10}$, C(O)NHO, and $C(O)NR_{10}$; and where m, n, and o vary independently from 0 to 4 and q and r vary independently from 0 to 2; and where $R_{10}$ and $R_{11}$ are independently selected from alkyl, aryl, and heteroaryl.

Overview of Combinatorial Synthesis

Combinatorial library synthesis is typically performed on a solid support. See, for example, Lam et al. (1991) *Nature* 354:82–84; Houghten et al. (1991) *Nature* 354:84–86. A large number of beads or particles are suspended in a suitable carrier (such as a solvent) in a parent container. The beads, for example, are provided with a functionalized point of attachment for a chemical module. The beads are then divided and placed in various separate reaction vessels. The first chemical module is attached to the bead, providing a variety of differently substituted solid supports. Where the first chemical module includes 3 different members, the resulting substituted beads can be represented as $A_1$, $A_2$, and $A_3$.

The beads are washed to remove excess reagents and subsequently remixed in the parent container. This bead mixture is again divided and placed into various separate reaction vessels. The second chemical module is coupled to the first chemical module. Where the second chemical module includes 3 different members, $B_1$, $B_2$, and $B_3$, 9 differently substituted beads result: $A_1B_1$, $A_1B_2$, $A_1B_3$, $A_2B_1$, $A_2B_2$, $A_2B_3$, $A_3B_1$, $A_3B_2$, and $A_3B_3$. Each bead will have only a single type of molecule attached to its surface.

The remixing/redivision synthetic process can be repeated until each of the different chemical modules has been incorporated into the molecule attached to the solid support. Through this method, large numbers of individual compounds can be rapidly and efficiently synthesized. For instance, where there are 4 different chemical modules, and where each chemical module contains 20 members, 160,000 beads of different molecular substitution can be produced.

Combinatorial library synthesis can be performed either manually or through the use of an automated process. For the manual construction of a combinatorial library, a scientist would perform the various chemical manipulations. For the construction of a combinatorial library through an automated process, the various chemical manipulations will typically be performed robotically. For example, see U.S. Pat. No. 5,463,564.

Solid Supports

The synthesis of a 2,4-pyrimidinedione library can be performed on a solid support. "Solid support" includes an insoluble substrate that has been appropriately derivatized such that a chemical module can be attached to the surface of the substrate through standard chemical methods. Solid supports include, but are not limited to, beads and particles, such as peptide synthesis resins. For example, see Merrifield (1963) *J. Am. Chem. Soc.* 85:2149–2154; U.S. Pat. No. 4,631,211; and Geysen et al. (1984) *Proc. Natl. Acad. Sci. USA* 81:3998–4002.

Solid supports can consist of many materials, limited primarily by the capacity of the material to be functionalized through synthetic methods. Examples of such materials include, but are not limited to, polymers, plastics, resins, polysaccharides, silicon or silica based materials, carbon, metals, inorganic glasses and membranes. Preferred resins include Sasrin resin (a polystyrene resin available from Bachem Bioscience, Switzerland), and TentaGel S AC, TentaGel PHB, or TentaGel S $NH_2$ resin (polystyrene-polyethylene glycol copolymer resins available from Rapp Polymere, Tubingen, Germany).

The solid support can be purchased with suitable functionality already present such that a chemical module can be attached to the support surface (e.g., Novabiochem, Bachem Bioscience, Rapp Polymere). Alternatively, the solid support can be chemically modified such that a chemical module can be attached to the support surface. Grant (1992) *Synthetic Peptides. A User's Guide*, W. H. Freeman and Co; Hermkens et al. (1996) *Tetrahedron* 52:4527–4554. The choice of functionality used for attaching a molecule to the solid support will depend on the nature of the compound to be synthesized and the type of solid support. Examples of functionality present on the solid support that can be used to attach a chemical module, include, but are not limited to, alkyl or aryl halides, aldehydes, alcohols, ketones, amines, sulfides, carboxyl groups, aldehyde groups, and sulfonyl groups.

Preferably, the functional group on the solid support that permits the attachment of a chemical module will be an alcohol, an amine, an aldehyde, or a diol group. Gordon et al. (1994) *J. Med. Chem.* 37:1385–1401; Hermkens et al. (1996) *Tetrahedron* 52:4527–4554.

For certain combinatorial libraries, one can purchase a solid support with an existing, protected chemical module already attached. An example of such a support is FmocGly Sasrin, which is commercially available from Rapp Polymere. Typically, however, the first step of the combinatorial library synthesis is the attachment of a chemical module to the solid support through the existing functionality on the support surface. Examples of chemical reactions that can be used to attach a chemical module to the support include, but are not limited to, nucleophilic displacement of a halide or other leaving group, etherification of an alcohol, esterification of an alcohol, amidation of an amine, acetalization of an aldehyde, and ketalization of a ketone. Hermkens et al. (1996) *Tetrahedron* 52:4527–4554.

Preferably, the reaction used to attach the chemical module to the solid support will be an esterification of an alcohol, an amidation of an amine, or an acetalization of an aldehyde. For example, see Hermkens et al. (1996) *Tetrahedron* 52:4527–4554.

For the attachment of certain chemical modules to the solid support, masking of functionality that is not involved in the attachment process, but that is incompatible with the mode of attachment, may be necessary. A non-limiting example of this type of process is the esterification of an alcohol functionalized solid support, using a hydroxyl-substituted carboxylic acid as the coupling partner. Prior to the esterification reaction, the hydroxyl group of the carboxylic acid would be "protected" through alkylation, silylation, acetylation, or through some other standard method. Strategies for the use of masking or protecting groups have been well-described in the art, such as in Green (1985) *Protecting Groups in Organic Synthesis,* Wiley.

Nucleophilic Aromatic Substitution Reactions

Nucleophilic substitution reactions at aromatic carbon centers typically proceed too slowly to be of synthetic utility. Under 4 different scenarios, however, there are exceptions to this rule: 1) where an electron withdrawing group is either ortho or para to the leaving group; 2) where a strong base forms an aryne intermediate that is subject to nucleophilic attack; 3) where the nucleophile can donate an electron through a transfer mechanism; 4) where a diazonium salt is replaced. see March, "Advanced Organic Chemistry," John Wiley & Sons, New York, 1985. Of these 4 mechanisms, the first is the most utilized form.

Figure 7:
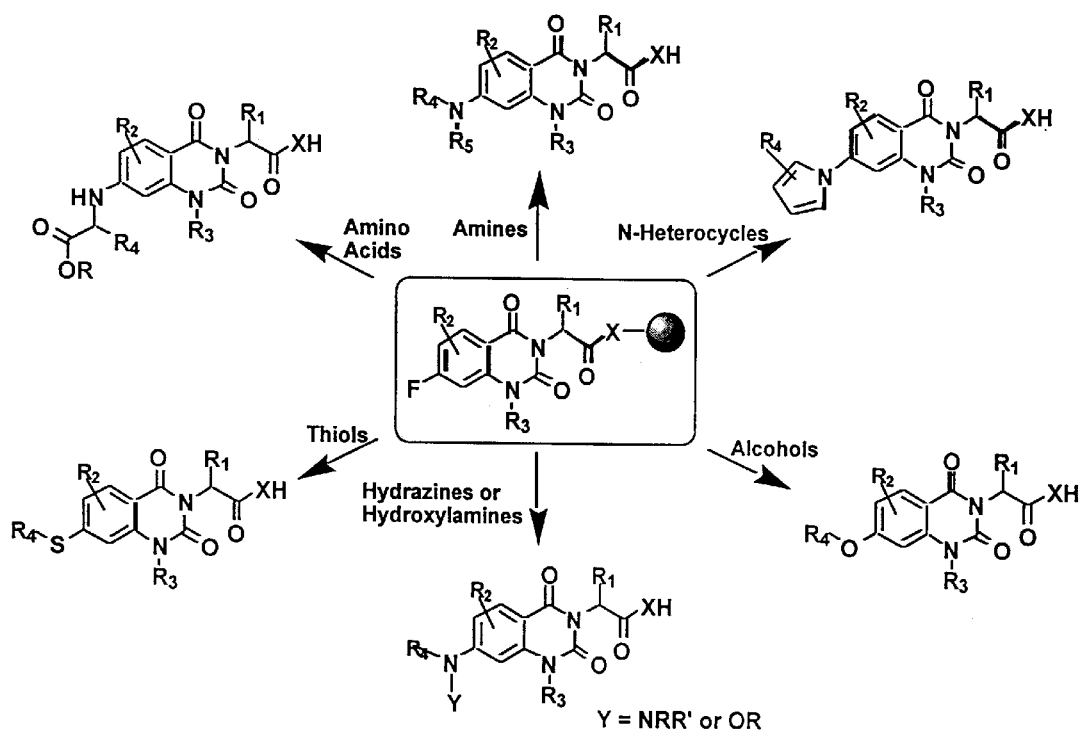
FIG. 7 illustrates the types of reagents that can be used to derivatize 7-fluoroquinazoline-2,3-diones through nucleophilic aromatic subsitution reactions.

The displacement of a fluoride substituent from an aromatic ring that contains a para carbonyl group is a version of the first nucleophilic aromatic substitution reaction mechanism. The carbonyl group can be an ester, ketone, heterocyclic vinylogous amide, or heterocyclic conjugated ketone. Luo et al. (1994) *J. Org. Chem.* 1761–1765; Berge et al. (1994) *Synlett* 187–188; Inoue et al. (1994) *J. Med. Chem.* 586–592; Cecchetti et al. (1993) *J. Het. Chem.* 1143–1148. Although 1 carbonyl group is sufficient to promote nucleophilic aromatic substitution, this reaction can be facilitated by the addition of a second or third electron withdrawing group to the aromatic ring. Examples of such electron withdrawing groups are shown in FIG. 7.

A variety of nucleophiles can be used to displace fluoride from an aromatic ring containing a para carbonyl group. Suitable nucleophilic reagents include, but are not limited to, amines, hydrazines, hydroxylamines, NH-heterocycles, alcohols, and thiols. Inoue et al. (1994) *J. Med. Chem.* 586–592; Cecchetti et al. (1993) *J. Het. Chem.* 1143–1148; Kalindjian et al. (1991) *Synlett* 803–804; Ziegler et al. (1988) *J. Het. Chem.* 1543; Cooper et al. (1992) *J. Med. Chem.* 1392–1398; Luo et al. (1994) *J. Org. Chem.* 1761–1765; Stabler et al. (1994) *Synth. Commun.* 123–129; Yeager et al. (1991) *Synthesis* 63–68; Berge et al. (1994) *Syntlett* 187–188; Guggenheim (1987) *Tetrahedron Lett.* 6139; Gornostaev et al. (1992) *Zh. Org. Khim.* 2291–2293.

Synthetic Routes to Fused 2,4-Pyrimidinedione Libraries

Figure 2:
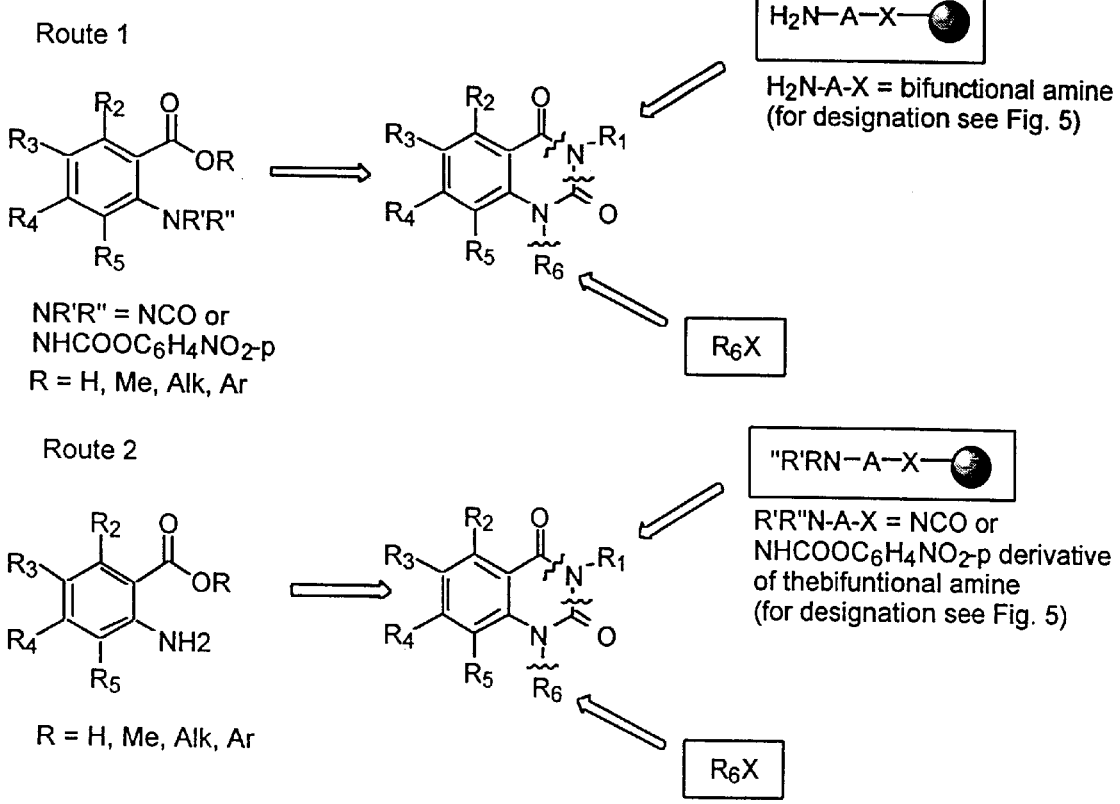
FIG. 2 illustrates general synthetic routes to fused 2,4-pyrimidinediones using solid support technology.

A general synthetic strategy for the construction of fused 2,4-pyrimidinedione containing libraries, delineating two possible synthetic routes, is shown in FIG. 2. The first route employs the addition of an immobilized amine derivative to an isocyanate or to an activated carbamate. The second route employs the addition of an aniline derivative to an immobilized isocyanate or to an immobilized activated carbamate.

To construct a 2,4-pyrimidinedione library through the immobilized amine derivative route, a chemical module containing a terminal amine, or protected terminal amine, is attached to a functionalized resin. Where the terminal amine of the chemical module is protected, the synthetic route proceeds through the deprotection of the terminal amine. An isocyanate or activated carbamate derived from an anthranilate or heterocyclic anthranilate is added to the immobilized amine to form a urea derivative. The urea derivative is treated with a base, producing a fused 2,4-pyrimidinedione attached to the solid support. Substitution of $N^1$ can be effected upon treatment of the immobilized, fused 2,4-pyrimidinedione with a base and an alkylating agent. Among other methods, such $N^1$-alkylation can also be achieved upon treatment of the immobilized fused 2,4-pyrimidinedione with an alcohol in the presence of a phosphine derivative and an alkyl azodicarboxylate. The fused 2,4-pyrimidinedione can be cleaved from the solid support, providing a fused 2,4-pyrimidinedione in solution.

Figure 3:
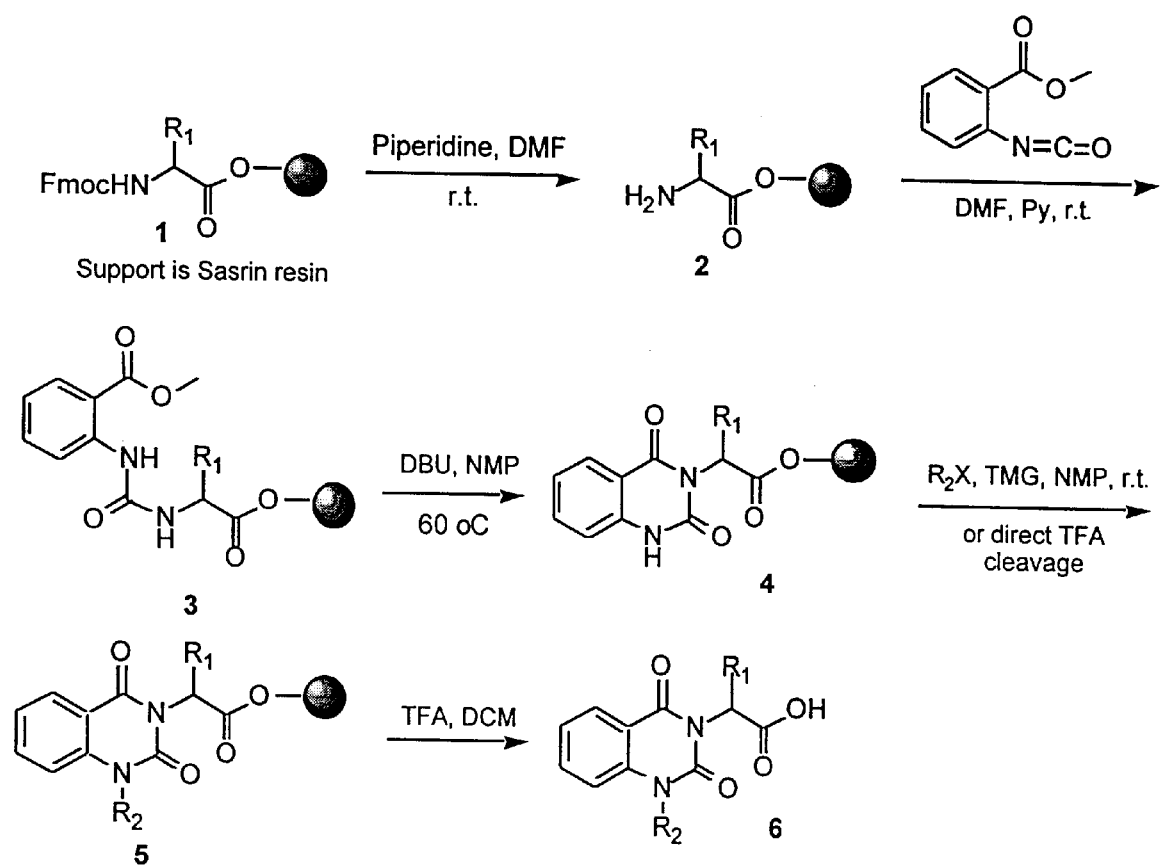
FIG. 3 illustrates a synthetic route to fused 2,4-pyrimidinediones, where an immobilized amine derivative is an intermediate in the synthesis, and where the cleavage of the 2,4-pyrimidinedione from the solid support provides a terminal carboxylic acid moiety.
Figure 4:
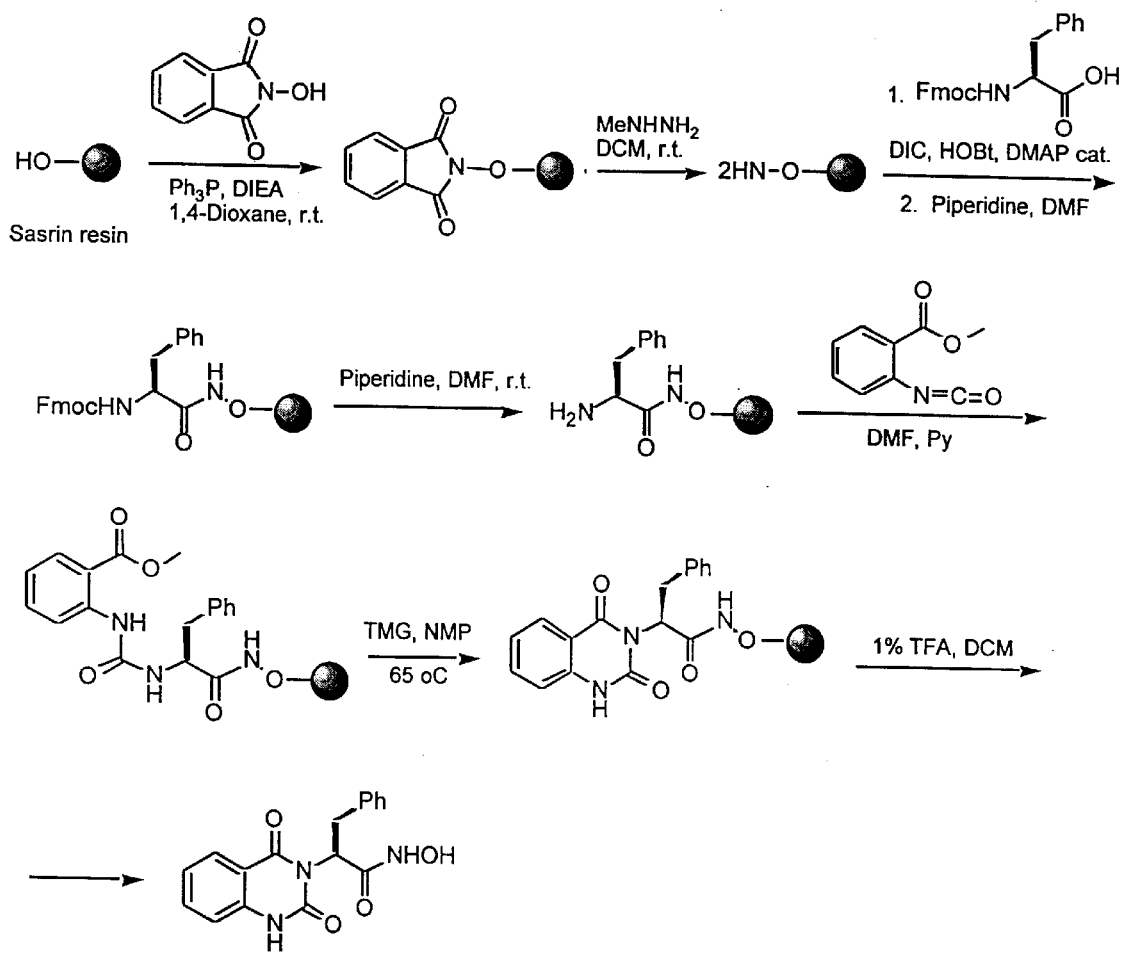
FIG. 4 illustrates a synthetic route to fused 2,4-pyrimidinediones, where an immobilized amine derivative is an intermediate in the synthesis, and where the cleavage of the 2,4-pyrimidinedione from the solid support provides a terminal hydroxamic acid moiety.

FIG. 3 shows a specific embodiment of the immobilized amine route, where the synthesized, fused 2,4-pyrimidinedione is a 2,4-quinazolinedione with an amino acid derived substituent at the 3-position. An Fmoc protected, amino acid modified, Sasrin resin is treated with piperidine to produce the unprotected, bound amino acid. To the bound amino acid is added 2-carboxymethyl phenylisocyanate. The resulting urea is cyclized upon treatment with DBU to form a solid support bound 2,4-quinazolinedione. This compound is alkylated upon the addition of an alkylating agent in the presence of a base. Cleavage of the synthesized compound is effected by treatment of the bound 2,4-quinazolinedione with triflouroacetic acid. FIG. 4 shows a slightly modified synthetic route for the construction of hydroxamic acids.

To construct a fused 2,4-pyrimidinedione library through the immobilized isocyanate or immobilized activated carbamate route, a chemical module containing a terminal amine, or protected terminal amine, is attached to a functionalized resin. Where the terminal amine of the chemical module is protected, the synthetic route proceeds through the deprotection of the terminal amine. The deprotected terminal amine is converted to either an isocyanate or to an activated carbamate. An anthranilate, anthranilic acid, heterocylic anthranilate or heterocyclic anthranilic acid is added to the isocyanate or activated carbamate, forming a urea derivative. The urea derivative is treated with a base, producing a fused 2,4-pyrimidinedione attached to the solid support. Substitution of $N^1$ can be effected upon treatment of the immobilized, fused 2,4-pyrimidinedione with a base and an alkylating agent. The fused 2,4-pyrimidinedione can be cleaved from the solid support, providing a 2,4-pyrimidinedione in solution.

Figure 5:
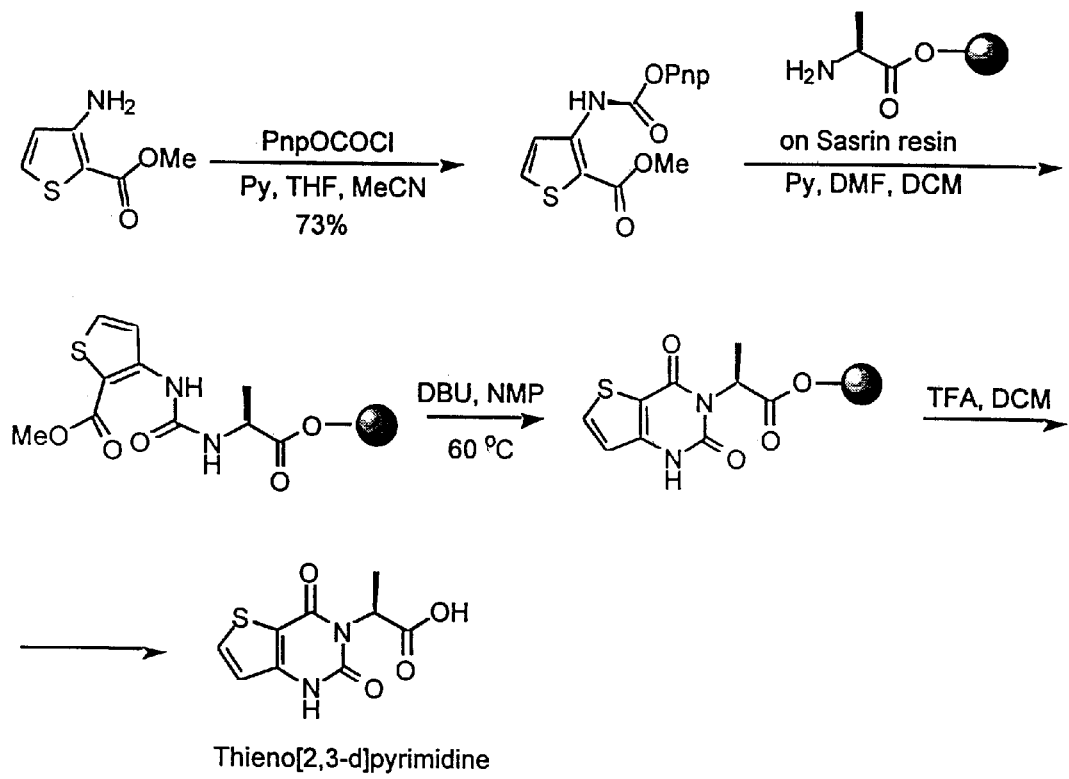
FIG. 5 illustrates a synthetic route to fused 2,4-pyrimidinediones, where an immobilized isocyanate derivative or an activated carbamate derivative is an intermediate in the synthesis.

FIG. 5 shows a specific embodiment of the immobilized isocyanate or immobilized activated carbamate route, where the synthesized, fused 2,4-pyrimidinedione is a 2,4-quinazolinedione with an amino acid derived substituent at the 3-position. An amino acid modified Sasrin resin is treated with either triphosgene and lutidine to produce the isocyanate, or with 4-nitrophenyl chloroformate and lutidine to produce the activated carbamate. Addition of methyl anthranilate to the isocyanate or the activated carbamate yields the corresponding urea. This urea is cyclized upon heating and treatment with DBU. The resulting bound 2,4-quinazolinedione is then cleaved by the addition of dilute trifluoroacetic acid.

Figure 6:
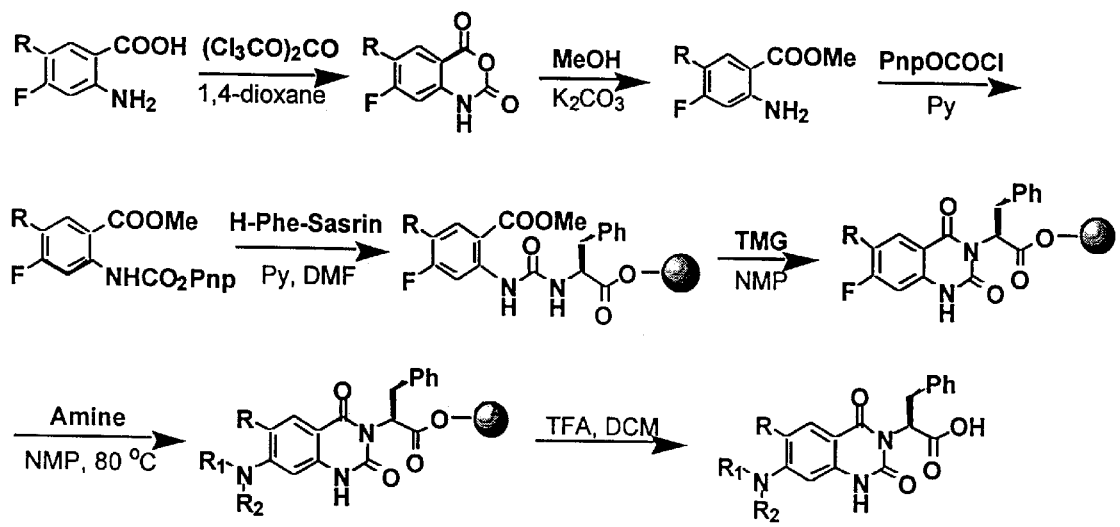
FIG. 6 illustrates a synthetic route to fused 2,4-pyrimidinediones, where 7-fluoroquinazoline-2,4-diones attached to a solid support are derivatized through nucleophilic aromatic substitution reactions.

FIG. 6 shows a specific embodiment of the immobilized amine route, where the substituent at the 7-position of the 2,4-quinazolinedione derivatives can be altered through the nucleophilic displacement of fluoride. An anthranilic acid derivative containing a fluoride substituent group para to the carboxylic acid is treated with triphosgene followed by potassium hydroxide in methanol to produce the corresponding methyl ester. The aniline group is converted to an activated carbamate upon treatment with 4-nitrophenyl chloroformate. Attachment of this intermediate is effected by reaction with H-Phe-Sasrin, which links the compound to the resin through the resultant urea functionality. The urea is cyclized upon treatment with base to form a 2,4-quinazolinedione derivative. Displacement of the fluoride substituent through nucleophilic displacement with an amine provides the desired solid support bound 2,4-quinazolinedione analogue. This analogue can be cleaved from the sasrin resin through treatment with trifluoroacetic acid.

A solid support bound, fused 2,4-pyridopyrimidine library can be recovered through conventional methods such as filtration or centrifugation. Confirmation that the solid support contains the desired fused 2,4-pyridopyrimidine compound can be accomplished by cleaving the fused 2,4 pyridopyrimidine from a small portion of the solid support, and then subjecting the cleaved product to conventional analysis. Examples of commonly used analytical methods include, but are not limited to, nuclear magnetic resonance spectroscopy and high performance liquid chromatography.

Methods of Cleavage

In one embodiment of the invention, the fused 2,4-pyrimidinedione library is bound to a solid support. In another embodiment of the invention, the fused 2,4-pyrimidinedione is cleaved from the solid support to produce soluble fused 2,4-pyrimidinedione libraries. Soluble libraries can be advantageous for a variety of purposes, including assaying the biological activity of compounds and performing structural analysis of compounds.

The cleavage of compounds from a solid support to produce a soluble chemical library can be accomplished using a variety of methods. For example, a compound can be photolytically cleaved from a solid support (Wang et al. (1976) *J. Org. Chem.* 41:3258; Rich et al. (1975) *J. Am. Chem. Soc.* 97:1575–1579), and through nucleophilic attack (U.S. Pat. No. 5,549,974), or through hydrolysis (Hutchins et al. (1994) *Tetrahedron Lett.* 35:4055–4058).

Preferably, the cleavage of compounds from a solid support to produce a soluble chemical library is accomplished using hydrolytic conditions, such as through the addition of dilute trifluoroacetic acid.

Screening

The present invention is directed toward the generation of fused 2,4-pyrimidinedione libraries. These libraries are used to select one or more fused 2,4-pyrimidinedione species that demonstrate a specific interaction with a targeted cellular ligand including, but not limited to, enzymes or receptors. A cellular ligand is targeted when it is believed that the ligand is of importance in the modulation of a disease. Examples of disease states for which fused 2,4-pyrimidinedione libraries can be screened include, but are not limited to, inflammation, infection, hypertension, CNS disorders, and cardiovascular disorders.

Several methods have been developed in recent years to screen libraries of compounds to identify the compounds having the desired characteristics. Typically, where a compound exhibits a dissociation constant of $10^{-6}$ or less when combined with the targeted enzyme or receptor, the compound is thought to demonstrate a specific interaction with the enzyme or receptor. Methods for isolating library compound species that demonstrate desirable affinity for a receptor or enzyme are well-known in the art.

For example, an enzyme solution may be mixed with a solution of the compounds of a particular combinatorial library under conditions favorable to enzyme-ligand binding. See Bush et al. (1993) *Antimicrobial Agents and Chemotherapy* 37:851–858, and Daub et al. (1989) *Biochemistry* 27:3701–3708. Specific binding of library compounds to the enzyme may be detected by any of the numerous enzyme inhibition assays which are well known in the art. Compounds which are bound to the enzyme may be readily separated from compounds which remain free in solution by applying the solution to a Sephadex G-25 gel filtration column. Free enzyme and enzyme-ligand complexes will pass through the column quickly, while free library compounds will be retarded in their progress through the column. The mixture of enzyme-ligand complex and free enzyme can then be treated with a powerful denaturing agent, such as guanidinium hydrochloride or urea, to cause release of the ligand from the enzyme. The solution can then be injected onto an HPLC column (for example, a Vydac C-4 reverse-phase column, eluted with a gradient of water and acetonitrile ranging from 0% acetonitrile to 80% acetonitrile). Diode array detection can provide discrimination of the compounds of the combinatorial library from the enzyme. The compound peaks can then collected and subjected to mass spectrometry for identification.

An alternate manner of identifying compounds that inhibit an enzyme is to divide the library into separate sublibraries where one step in the synthesis is unique to each sublibrary. To generate a combinatorial library, reactants are mixed together during a step to generate a wide mixture of compounds. At a certain step in the synthesis, however, the resin bearing the synthetic intermediates can be divided into several portions, with each portion then undergoing a unique transformation. The resin portions are then (separately) subjected to the rest of the synthetic steps in the combinatorial synthetic method. Each individual resin portion thus constitutes a separate sublibrary. When testing the compounds, if a given sublibrary shows more activity than the other sublibraries, the unique step of that sublibrary may then be held fixed. The sublibrary then becomes the new library, with that step fixed, and forms the basis for another round of sublibrary synthesis, where a different step in the synthesis is optimized. This procedure can be executed at each step until a final compound is arrived at. The aforementioned method is the generalization of the method described in Geysen, WO 86/00991, for determining peptide "mimotopes," to the synthetic method of this invention.

Finding a compound that inhibits an enzyme is most readily performed with free compound in solution. The compounds can also be screened while still bound to the resin used for synthesis; in some applications, this may be the preferable mode of finding compounds with the desired characteristics. For example, if a compound that binds to a specific antibody is desired, the resin-bound library of compounds may be contacted with an antibody solution under conditions favoring a stable antibody-compound-resin complex. A fluorescently labeled second antibody that binds to the constant region of the first antibody may then be contacted with the antibody-compound-resin complex. This will allow identification of a specific bead as carrying the compound recognized by the first antibody binding site. The bead can then be physically removed from the resin mixture and subjected to mass spectral analysis. If the synthesis has been conducted in a manner such that only one compound is likely to be synthesized on a particular bead, then the binding compound has been identified. If the synthesis has been carried out so that many compounds are present on a single bead, the information derived from analysis can be utilized to narrow the synthetic choices for the next round of synthesis and identification.

The enzyme, antibody, or receptor target need not be in solution either. Antibody or enzyme may be immobilized on a column. The library of compounds may then be passed over the column, resulting in the retention of strongly binding compounds on the column after weaker-binding and non-binding compounds are washed away. The column can then be washed under conditions that dissociate protein-ligand binding, which will remove the compounds retained in the initial step. These compounds can then be analyzed, and synthesized separately in quantity for further testing. Similarly, cells bearing surface receptors can be expressed on a cell surface may be contacted with a solution of library compounds. The cells bearing bound compounds can be readily separated from the solution containing non-binding compounds. The cells can then be washed with a solution which will dissociate the bound ligand from the cell surface receptor. Again, the cells can be separated from the solution, and the solutio The following examples are provided to illustrate, but not limit, the invention.

EXAMPLES

General Methods

Reagents were purchased from Aldrich, Sigma, Bachem Biosciences and Rapp Polymere and used without further purification. Immobilized N-Fmoc-protected amino acids were prepared from commercial Fmoc-amino acids using standard coupling protocols, (Grant (1992) *Synthetic Peptides. A User's Guide.* W. H. Freeman and Co.) or purchased from Bachem Bioscience.

After workup, concentration of solutions was performed by reduced pressure rotary evaporation, or using the Savant's SpeedVac instrument.

NMR spectra were recorded on a Varian Gemini 300 Mhz instrument with $CDCl_3$ as solvent unless noted. $^1H$ NMR data are reported as follows: chemical shifts relative to tetramethylsilane (0.00 ppm), multiplicity (s=singlet, d=doublet, dd=doublet of doublets, t=triplet, m=multiplet), coupling, and integration. Assignment of protons was aided by decoupling experiments. Mass-spectra were obtained using ESI technique. HPLC analysis and purification were performed using Beckman System Gold$^R$; detection at 220 nm. Analytical HPLC was performed on Rainin Microsorb C18 (4.6 mm×150 mm) reverse phase column (gradient from 100% of the aq. 0.1% TFA to 100% of 0.1% TFA in MeCN over 35 min, flow rate 1.0 mL/min). For the 7-substituted 2,4-quinazolinediones, analytical HPLC was performed on YMC 4.6×500 mm reverse phase column using a gradient from 90% of the aq. 0.1% TFA (eluent A)—10% of 0.1% TFA in MeCN (eluent B) to 100% of the eluent B over 6 min., flow rate 2.0 mL/min.

General Procedures for Solid Phase Preparations of $N^1$-Unsubstituted Fused 2,4-Pyrimidinediones Method A. From Immobilized Amine Reagents with Isocyanates or Activated Carbamates in Solution An appropriate N-Fmoc-protected amino acid resin [0.06 mmol, ca. 100 mg for the Sasrin support immobilized amines] was deprotected with 20% piperidine in dimethylformamide for 30 min. The resin was filtered, washed liberally with dimethylformamide, MeOH, and $CH_2Cl_2$, and dried under vacuum. The amine resin was suspended with an appropriate isocyanate or p-nitrophenylcarbamate (0.2–0.5 mmol) in 10% pyridine in dimethylformamide (1–2 mL), and agitated at room temperature (r.t.). until a negative ninhydrine test indicated the absence of a free amine on a solid phase (typically, 0.5–3 h for reactions with isocyanates, or 1–24 h for reactions with p-nitrophenylcarbamate). The resultant urea resin was filtered, washed liberally with dimethylformamide, MeOH, and $CH_2Cl_2$, and dried under vacuum. Immobilized urea derivatives thus obtained were further cyclized into fused 2,4-pyrimidinediones by agitation at 40–80° C. (preferably at 50–65° C.) with an organic (such as 2–10% 1,8-diaza-bycyclo[5.4.0]undec-7-ene, 1,4-diazabycyclo[2.2.2]octane, 1,5-diazabycyclo[4.3.0]-non-5-ene, or tetramethylguanidine in dimethylformamide, N-methylpyrrolidine-2-one, and like polar solvents) or inorganic (such as 1–10% lithium, sodium, or cesium carbonates in dimethylformamide or N-methylpyrrolidine-2-one) bases for 2–24 h. The resin was filtered, washed liberally with dimethylformamide, MeOH, and $CH_2Cl_2$, and dried under vacuum. The resultant fused 2,4-pyrimidinediones were cleaved from supports with 1–40% TFA in $CH_2Cl_2$ for 0.5–2 h. Thus, the Sasrin resin immobilized products were typically released from support with 1% TFA in $CH_2Cl_2$ (30 min). When necessary, amino acid side chain functionalities were further deprotected with mixtures of TFA and additives (scavengers: thiols, phenols, or trialkylsilanes), such as 5% triethylsilane –40% TFA in $CH_2Cl_2$ (0.5–4 h, depending on the nature of the protection groups). The crude products were lyophilized and analyzed by NMR, MS, and HPLC.

Method B. From Immobilized Isocyanates with Amine Reagents in Solution

An appropriate amine resin (such as immobilized amino acid reagents, see above, Method A; 0.06 mmol, ca. 100 mg for Sasrin support) was agitated with triphosgene (60 mg, 0.19 mmol) and organic base (such as 2,6-lutidine, 0.3 ml) in $CH_2Cl_2$ (1.5 ml) for 0.5–1.5 h (until a negative ninhydrin test indicated the absence of a free amine on a solid phase). The resultant isocyanate resin was washed liberally with $CH_2Cl_2$, and an appropriate amine (such as methyl anthranilate, 1 mmol) with 2,6-lutidine (0.2 ml) in $CH_2Cl_2$ (2 ml) was added. The mixture was agitated at r.t. until the reaction was completed (typically, 2–8 h). The resin was filtered, washed liberally with dimethylformamide, MeOH, and $CH_2Cl_2$, and dried under vacuum. The resultant immobilized ureas were further converted into fused 2,4-pyrimidinediones analogously to the Method A.

Method C. From Immobilized Activated Carbamates with Amine Reagents in Solution

An appropriate amine resin (such as immobilized amino acid reagents, see above, Method A; 0.06 mmol, ca. 100 mg for Sasrin support) was agitated with p-nitrophenyl chloroformate (202 mg, 1.0 mmol) and organic base (such as 2,6-lutidine, 0.3 ml) in $CH_2Cl_2$ (1.5 ml) for 1–2 h (until a negative ninhydrin test indicated the absence of a free amine on a solid phase). The resultant p-nitrophenylcarbamate resin was filtered, washed liberally with $CH_2Cl_2$, dried under vacuum (r.t., 0.5 Torr). An appropriate amine (such as methyl anthranilate, 1 mmol) and a solution of organic base such as 10% pyridine or 2,6-lutidine in dimethylformamide (2 ml) was added, and the mixture agitated at 20–70 ° C for 8–24 h (typically, this reaction with methyl anthranilates was essentially completed overnight at r.t.). The resin was filtered, washed liberally with dimethylformamide, MeOH, and $CH_2Cl_2$, and dried under vacuum. The resultant immobilized ureas were further converted into fused 2,4-pyrimidinediones analogously to the Method A.

3-[(S)-1-Benzyl-1-carboxymethyl]-2.4-(1H, 3H1)-quinazolinedione.

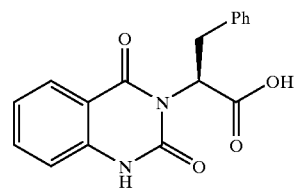

The compound was prepared from the Fmoc-Phe-Sasrin resin with 2-methoxycarbonylphenylisocyanate (Method A), or with triphosgene and methyl anthranilate (Method B), or with p-nitrophenyl chloroformate and methyl anthranilate (Method C) of the General Procedures for Solid Phase Preparations of Fused 2,4-Pyrimidinediones. HPLC purity 94%. $R_t$ 14.0. $^1H$ NMR in $CDCl_3$ (δ, ppm): 3.35 (m, 2H), 5.68 (m, 1H), 6.84 (d, J=8.7 Hz, 1H), 6.90–7.02 (m, 6H), 7.38 (m, 1H), 7.83 (d, J=8.7 Hz, 1H), 9.97 (br. s, 1H). Mass-spectrum (m/z): 311 $(M+H)^+$.

3-[(S)-1-Carboxyethyl]-2.4-(1H, 3H)-thieno[2.3-d]pyrimidinedione

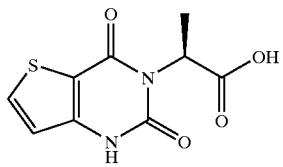

The compound was prepared from the FmocAla-Sasrin resin with 3-(p-nitrophenyl)carbamoyl-2-methoxycarbonylthiophene (Method A) of the General Procedures for Solid Phase Preparations of Fused 2,4-Pyrimidinediones. HPLC purity 94%. $R_t$ 15.6 min. $^1$H NMR in $CD_3OD$ (δ, ppm): 1.57 (d, J=6.9 Hz, 3 H), 5.53 (m, 1H), 6.94 (d, J=5.1 Hz, 1H), 7.95 (d, J=5.1 Hz, 1H).

3-[(S)-1-Benzyl-1-[(S)-2-carbonylaminopropionic acid]methyl-2.4-(1H, 3 H)-quinazolinedione.

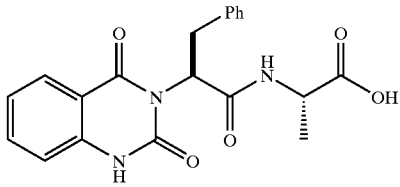

Commercial Fmoc-Ala-Sasrin resin (0.06 g, ca. 0.036 mmol) was deprotected by agitation with 20% piperidine in dimethylformamide (1 ml, 30 min at r.t.), filtered, washed liberally with dimethylformamide, MeOH, and $CH_2Cl_2$, and dried under vacuum. Fmoc-Phe-OH (0.172 g, 0.445 mmol), 1-hydroxybenzotriazole (0.068 g, 0.445 mmol), and diisopropylcarbodiimide (0.07 mL, 0.445 mmol) were mixed in N-methylpyrrolidine-2-one (1 ml), and the mixture stirred at r.t. for 20 min. The resultant solution was added to the above deprotected H-Ala-Sasrin, and the mixture agitated by gentle shaking for 1.5 h. The FmocPhe-Ala-Sasrin dipeptide resin thus obtained was deprotected by agitation with 20% piperidine in dimethylformamide (1 ml, 30 min at r.t.), filtered, washed liberally with dimethylformamide, MeOH, and $CH_2Cl_2$, and dried under vacuum. 2-Methoxycarbonylphenylisocyanate (0.089 g, 0.5 mmol) in 10% pyridine in dimethylformamide (1 ml) was added to the deprotected dipeptide amine resin, and the mixture agitated for 1 h. The resultant urea resin was filtered, washed liberally with dimethylformamide, MeOH, and $CH_2Cl_2$, dried under vacuum, and then cyclized by stirring at 60° C. with 5% tetramethylguanidine or 5% 1,8-diaza-bycyclo[5.4.0]undec-7-ene in N-methylpyrrolidine-2-one (1 ml) for 21 h. The resultant quinazolinedione resin was cleaved with 3% trilfluoroacetic acid in $CH_2Cl_2$, and the product was isolated and analyzed as described above (see the General Procedures for Solid Phase Preparations of $N^{1-}$-Unsubstituted Fused 2,4-Pyrimidinediones). HPLC purity 90%. $R_t$ 16.3. $^1$H NMR in $CD_3OD$ (δ, ppm): 1.33 (d, J=7.5 Hz, 3H), 3.40–3.60 (m, 2H), 4.48 (m, 1H), 5.82 (m, 1H) 7.00–7.20 (m, 7H), 7.58 (m, 1H), 7.90 (dd, J=7.8 and 1.2 Hz, 1H).

Table 1. Other Cleaved $N^1$—H Quinazolinediones made using the immobilized amine method, where $R_1$ is an amino acid derivative.

TABLE 1

| | Cleaved $N^1$-H Quinozalinediones 5* | |
|---|---|---|
| Entry # | Amino Acid | HPLC Purity for Products 5, % |
| 1 | Ala | 95 |
| 2 | Val | 90 |
| 3 | Ile | 81 |
| 4 | Met | 92 |
| 5 | Phe | 94 |
| 6 | Tyr($^t$Bu) | 97 |
| 7 | Asp($^t$Bu) | 92 |
| 8 | Glu($^t$Bu) | 93 |
| 9 | Arg(Mtr) | 95 |
| 10 | Lys(Boc) | 85 |
| 11 | Trp(Boc) | 92 |

*Cleaved with 1% TFA in DCM. No $N^1$-alkylation was performed Structures were in agreement with NMR and MS data.

General Procedures for Solid Phase Preparations of $N^1$-Alkylated Fused 2, 4-Pyrimidinediones Method A. From Alkyl Halides An appropriate $N^1$-H quinazolinedione resin was prepared as discussed above (0.06 mmol, ca. 100 mg for Sasrin support) was agitated with appropriate alkylating reagents (1.2 mmol) and organic base (such as tetramethylguanidine, 1,8-diazaby-cyclo[5.4.0]undec-7-ene and alike, 1.2 mmol) in N-methylpyrrolidine-2-one (1.75 ml) for 10–48 h at 20–70° C.(typically, 18 h at r.t. for examples given in the Table 2). The resultant resin was filtered, washed liberally with $CH_2Cl_2$, MeOH, and dried under vacuum (r.t., 0.5 Torr). Cleavage and isolation of the $N^1$-alkylated quinazolinediones was performed as described above for preparations of $N^1$-H quinazolinediones (see Method A).

Method B. From Alcohols

An appropriate $N^1$-H quinazolinedione resin was prepared as discussed above in General Procedures for Solid Phase Preparations of $N^1$-Unsubstituted Fused 2,4-Pyrimidinediones (0.06 mmol, ca. 100 mg for Sasrin support) with an appropriate alcohol (2.4 mmol), trisubstituted phosphine (such as triphenylphosphine, 0.472 g, 1.8 mmol), and dialkyl azodicarboxylate (such as diisopropyl azodicarboxylate, 0.283 mL, 1.8 mL) in aprotic organic solvent (such as 1,4-dioxane, 3.6 mL) was agitated at r.t. for 4–24 h (typically overnight). The resultant resin was filtered, washed liberally with $CH_2Cl_2$, MeOH, and dried under vacuum (r.t., 0.5 Torr). Cleavage and isolation of the $N^1$-alkylated quinazolinediones was performed as described above for preparations of $N^1$-H quinazolinediones (see above, Method A).

3-[(S)-1-Benzyl-1-carboxymethyl]-1-methyl-2,4-(1H, 3H)-quinazolinedione

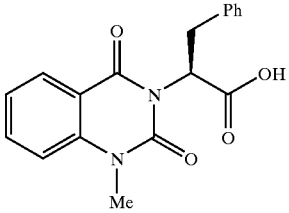

The compound was prepared from the Fmoc-Phe-Sasrin resin via alkylation of the Sasrin support immobilized 3-[(S)-1-benzyl-1-carboxymethyl]-2,4-(1H, 3H)-quinazolinedione (see the example described above) according to Method A and Method B of the General Procedures for Solid Phase Preparations of $N^1$-Alkylated Fused 2,4-

Pyrimidinediones. $^1$H NMR in CD$_3$OD ($\delta$, ppm): 3.25–3.58 (m, 2H), 3.51 (s, 3H), 5.89 (m, 1H), 7.00–7.20 (m, 5H), 7.26 (m, 1H), 7.37 (d, J=9.0 Hz, 1H), 7.73 (dd, J=7.2, 8.4 Hz, 1H), 8.02 (d, J=7.5 Hz, 1H). Mass-spectrum (m/z): 325 (M+H)$^+$.

3-[(S)-1-Benzyl-1-carboxymethyl]-1-(p-methoxy)benzyl-2,4-(1H, 3H)-quinazolinedione.

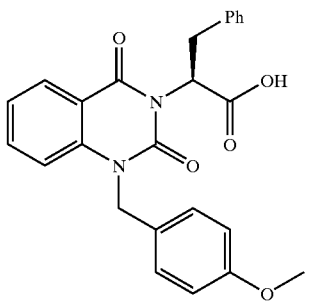

The compound was prepared from the Fmoc-Phe-Sasrin resin via alkylation of the Sasrin support immobilized 3-[(S)-1-benzyl-1-carboxymethyl]-2,4-(1H, 3H)-quinazolinedione (see the example described above) according to Method A and Method B of the General Procedures for Solid Phase Preparations of N$^1$-Alkylated Fused 2,4-Pyrimidinediones. $^1$H NMR in CD$_3$OD ($\delta$, ppm): 3.56 (m, 2H), 4.89 (s, 3H), 5.08 (d, J=16.2 Hz, 1H), 5.37 (d, J=16.2 Hz, 1H), 6.00 (m, 1H), 6.82 (d, J=8.4 Hz, 2H), 6.90–7.23 (m, 7H), 7.56 (dd, J=8.4 and 7.2 Hz, 1H), 8.03 (d, J=8.1 Hz, 1H). Mass spectrum (m/z): 431 (M+H)$^+$.

Table 2. Other alkylated quinazolinediones made according to Method A and Method B.

TABLE 2

Quinozalinediones 6 made from Phe

| Entry # | R$_2$X | HPLC Purity for Products 6*, % |
|---|---|---|
| 1 | MeI | 88 |
| 2 | BrCH$_2$CH$_2$OCH$_2$CH$_2$OMe | 75 |
| 3 | ClCH$_2$Ph | 94 |
| 4 | ICH$_2$(CH$_2$)$_4$Me | 99 |
| 5 | 2-BrCH$_2$-Naphthalene | 99 |
| 6 | N-(BrCH$_2$CH$_2$CH$_2$)-Phthalimide | 97 |
| 7 | BrCH$_2$C$_6$H$_4$OMe-p | 94 |
| 8 | BrCH$_2$C$_6$H$_4$NC-o | 91 |
| 9 | BrCH$_2$CO$_2$$^t$Bu | 93 |
| 10 | BrCH$_2$CONH$_2$ | 93 |

*Cleaved with 1% TFA in DCM.

General Procedure for Solid Phase Preparations of the Fused 2,4-Pyrimidinedione Hydroxamate Derivatives Diisopropyl azodicarboxylate (1.75 ml, 8.90 mmol) was added under inert atmosphere at ca. 10° C. to the mixture of an appropriate alcohol resin (such as Sasrin resin, 1.0 g, 89 mmol) with N-hydroxyphthalimide (1.45 g, 0.89 mmol) and triphenylphosphine (2.33 g, 8.90 mmol) in 1,4-dioxane (30 ml), and the mixture agitated for 24 h. Alternatively, haloalkyl-functionalized resin (such as chlorotrityl resin, 1.00 g, 0.67 mmol) was agitated with N-hydroxyphthalimide 1.10 g, 6.8 mmol) and diisopropylethylamine (2.36 ml, 13.6 mmol) in 1,4-dioxane (20 ml) and CH$_2$Cl$_2$ (4 ml) for ca. 17 h. The resin was filtered, washed liberally with CH$_2$Cl$_2$, MeOH, and dried under vacuum (r.t., 0.5 Torr). The resulted O-immobilized- N-hydroxyphthalimide resins were agitated with methylhydrazine (0.47 ml, 8.9 mmol) in CH$_2$Cl$_2$ (18 ml) for 24 h, filtered, washed liberally with CH$_2$Cl$_2$, MeOH, and dried under vacuum (r.t., 0.5 Torr). The O-immobilized hydroxylamine supports thus obtained were coupled with appropriate N-Fmoc-protected amino acids under standard conditions, (Grant (1992) Synthetic Peptides. A User's Guide. W. H. Freeman and Co.) and the resultant immobilized amino hydroxamic acids were employed in the preparation of the fused 2,4-pyrimidinedione hydroxamate derivatives in a manner similar to syntheses of fused 2,4-pyrimidinediones with terminal carboxylic functionalities (see the General Procedures for Solid Phase Preparations of Fused 2,4-Pyrimidinediones).

3-[(S)-1-Benzyl-1-hydroxamidomethyl]-2,4-(1H, 3H)-quinazolinedione

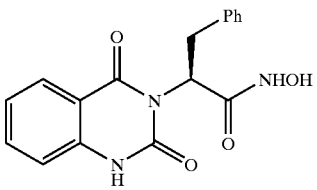

The compound was prepared from FmocPhe-OH and the O-immobilized hydroxylamine support resin (made from the Sasrin resin as described above, see General Procedure for Solid Phase Preparations of the Fused 2,4-Pyrimidinedione Hydroxamate Derivatives). The crude reaction product was purified by preparative TLC (the major FeCl$_3$-positive spot; eluent: CH$_2$Cl$_2$—MeOH 6:1). Mass-spectrum (m/z): 324 (M–H)$^-$.

Preparation of Intermediates for the Solid Phase Synthesis of 7-Substituted Quinazoline-2,4-diones Methyl 4,5-Difluoroanthranilate

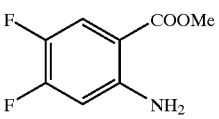

Triphosgene (0.65 g, 0.22 mmol) was added to 4,5-difluoroanthranilic acid (0.34 g, 0.2 mmol) in dry 1,4-dioxane (30 ml), and the mixture was stirred at rt. for 1 h. Solvent was slowly distilled off at ca. 50° C., and the residue distributed between ethyl acetate (100 ml) and the pH 7 buffer (50 ml). The aqueous layer was extracted with more ethyl acetate (2×50 ml), and combined organic layers washed with diluted aq. citric acid (pH ca. 4–5), water (30 ml), brine (50 ml), and dried (MgSO$_4$). Solvent was removed in vacuo to yield 0.33 g (83%) of 6,7-difluoroisatoic anhydride. The intermediate thus obtained (0.29 g, 1.45 mmol) was stirred with dry potassium carbonate (0.20 g, 1.45 mmol) in dry methanol (30 ml) for 1 h. Most of the solvent was removed in vacuo, and the residue distributed between ethyl acetate (100 ml) and the pH 7 buffer (50 ml). Aqueous layer was adjusted to pH ca. 7 with additional aq. HCl, and extracted with ethyl acetate (2×30 ml). Combined organic layers were washed with water (2×30 ml), brine (50 ml), and dried (MgSO$_4$). Solvent was removed in vacuo to yield 0.24 g (89%) of methyl 4,5-difluoroanthranilate. $^1$H NMR in CDCl$_3$ ($\delta$,ppm): 3.86 (s, 3 H), 5.72 (br. s, 2 H), 6.43 (m, 1 H), 7.66 (m, 1 H).

Methyl 2-(p-Nitrophenyl)carbamoyl-4,5-difluorobenzoate

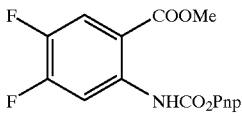

Methyl 4,5-difluoroanthranilate (0.19 g, 1 mmol) in THF (1.5 ml) was added at ca. 0° C. to p-nitrophenyl chloroformate (0.21 g, 1.05 mmol) in pyridine (0.089 ml, 1.1 mmol) and dry acetonitrile (2.0 ml). The mixture was stirred at r.t. for 2 h. Solvent was removed in vacuo, and the residue triturated with ethyl ether (ca. 3 ml), filtered, washed with ether (2×2 ml), water (3×3 ml), hexanes (3×5 ml), and dried in vacuo. Yield 0.27 g (77%). $^1$H NMR in CDCl$_3$ ($\delta$,ppm): 3.98 (s, 3 H), 7.40 (d, J=8.1 Hz, 2 H), 7.90 (m, 1 H), 8.30 (d, J 8.1 Hz, 2 H), 8.38 (m, 1 H), 11.07 (s, 1 H).

Methyl 4-Fluoroanthranilate Hydrochloride

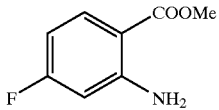

Triphosgene (3.26 g, 11 mmol) was added to 4-fluoroanthranilic acid (1.55 g, 1.0 mmol) in dry 1,4-dioxane (50 ml), and the mixture was stirred at rt. for 1 h, and then 50° C. for ca. 30 min. Solvent was removed in vacuo, dry methanol (30 ml) added, followed by potassium carbonate (4.42 g, 35 mmol). The mixture was stirred at r.t. for 30 min, and then 2.5 h at 50° C. Inorganic material was filtered off, and the residue distributed between ethyl acetate (150 ml) and the pH 7 buffer (75 ml). Aqueous layer was extracted with ethyl acetate (2×50 ml). Combined organic layers were washed with water diluted aq. sodium bicarbonate (pH ca. 8; 2×50 ml), brine (50 ml), and dried (MgSO$_4$). The organic solution was concentrated in vacuo (to ca. 75 ml), and 1 M hydrogen chloride in ethyl ether (ca. 25 ml) added. The precipitated crystalline product was filtered off, washed with ethyl ether, hexanes, and dried in vacuo. Yield 1.00 g (49%). $^1$H NMR in 5% CD$_3$OD in CDCl$_3$ ($\delta$, ppm): 3.83 (s, 3 H), 6.55 (m, 1 H), 6.66 (m, 1 H), 7.88 (m, 1 H).

Methyl 2-(p-Nitrophenyl)carbamoyl-4-fluorobenzoate

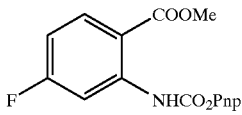

Pyridine (0.36 ml, 4.4 mmol) was added dropwise with stirring to the mixture of methyl 4-fluoroanthranilate hydrochloride (0.41 g, 2 mmol) and p-nitrophenylchloroformate (0.424 g, 2.1 mmol) in dry acetonitrile (7 ml). The mixture was stirred for 1.5 h at r.t. and evaporated. The residue was triturated with acetonitrile (1.5 ml), filtered, washed with ethyl ether (3×2 ml), acetonitrile (0.5 ml), ether (2 ml), and dried in vacuo. Yield 0.64 g (96%). $^1$H NMR in CDCl$_3$ ($\delta$,ppm): 3.97 (s, 3 H), 6.85 (m, 1 H), 7.42 (d, J32 8.1 Hz, 2 H), 8.11 (m, 1 H), 8.22 (m, 1 H), 8.29 (d, J=8.1 Hz, 2 H), 11.23 (s, 1 H).

Table 3. Selected Examples 7-Substituted Quinazoline-2,4-diones Made Through Nucleophilic Aromatic Substitution

TABLE 3

7-Fluoroquinazolinediones*

Structure: quinazoline-2,4-dione core with $R_1$ at 6-position, $R_2$-N-$R_2$ at 7-position, and N-substituted with CH(CH$_2$Ph)COOH (phenylalanine residue) at N-3.

| Entry # | $R_1$ | Amine Substituent | HPLC purity, % (220 nm) |
|---|---|---|---|
| 1 | H | Me—N(piperazine)NH | 80 |
| 2 | F | cyclohexyl-CH$_2$—NH$_2$ | 97 |
| 3 | F | cyclohexyl-CH$_2$—NH$_2$ | 97 |
| 4 | F | phenyl-CH$_2$—NH$_2$ | 95 |
| 5 | F | HN(piperazine)NH | 96 |

\* See FIG. 6.
\*\*Structures are in agreement with $^1$H NMR and MS data.

General Procedure for Solid Phase Synthesis of 7-Substituted Quinazoline-2,4-diones 7-Fluoroquinazoline-2,4-dione Sasrin resin was prepared as we described previously in a prior patent application [Gordeev and Patel, Solid Phase and Combinatorial Syntheses of Fused 2,4-Pyrimidinediones, Ser. No. 08/740,103]. The above resin (ca. 0.03 mmol) was agitated with an appropriate nucleophilic reagent (such as amine, 0.9 mmol) in N-methylpyrrolidine-2-one (1.25 ml) with or base (such as triethylamine, diisopropylamine, tetraalkylguanidine, 1,8-diazabicyclo[5.4.0]undec-7-ene and alike) at 50–120° C. for 2–36 h until the reaction was complete by gel-phase $^{19}$F NMR of the resin; typically, 4–6 h for reactions of amines with 6,7-difluoroquinazolinedione resins; no addition of a base was required for preparation of compounds listed below and in the Table 2). This transformation with other nucleophilic reagents, such as thiols, alcohols, or NH-heterocycles is performed in polar organic solvents, such as pyridine, N-methylpyrrolidine-2-one, dimethylformamide, dimethylacetamide, acetonitrile, dimethylsulfoxide, sulfolan, tetrahydrofuran and alike, with or without addition of base (such as organic bases: triethylamine, diisopropylamine, tetraalkylguanidine, 1,8-diazabicyclo[5.4.0]undec-7-ene, or metal amides; or inorganic bases, such as alkali metal carbonates, sodium hydride, etc.), at 50–120° C. for 2–36 h. Resin after reaction was filtered, washed liberally with methanol and CD$_2$Cl$_2$, and dried in vacuo. Cleavage of the resin and product isolation were performed as described above.

3-[(S)-1-Benzyl-1-carboxymethyl]-7-[(4-methyl)-1-piperazino]-2,4-(1 H, 3 H)-quinazolinedione

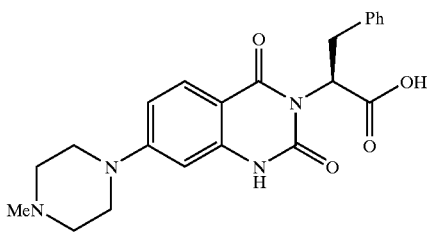

The product was prepared from Fmoc-Phe-Sasrin, methyl 2-(p-nitrophenyl)carbamoyl-4-fluorobenzoate, and 1-methylpiperazine as described above in the General Procedure for Solid Phase Synthesis of 7-Substituted Quinazoline-2,4-diones. $R_t$ 2.3 min. Mass-spectrum (m/z): 409 (M+H)$^+$.

3-[(S)-1-Benzyl-1-carboxymethyl]-6-fluoro-7-(1-piperazino)-2,4-(1H, 3H)-quinazolinedione

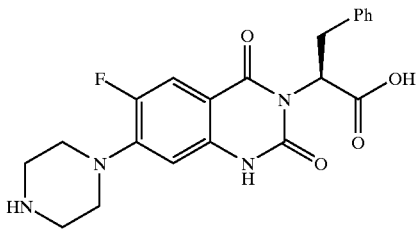

The product was prepared from Fmoc-Phe-Sasrin, methyl 2-(p-nitrophenyl)carbamoyl-4,5-difluorobenzoate, and piperazine as described above in the General Procedure for Solid Phase Synthesis of 7-Substituted Quinazoline-2,4-diones. $R_t$ 2.5 min. $^1$H NMR in 5% CD$_3$OD in CDCl$_3$ (δ,ppm): 3.28–3.43 (m, 9 H), 3.45–3.58 (m, 1H), 5.76 (m, 1 H), 6.49 (d, J=6.9 Hz, 1 H), 7.00–7.18 (m, 5 H), 7.48 (d, J=12.4 Hz, 1 H). Mass-spectrum (m/z): 413 (M+H)$^+$.

3-[(S)-1-Benzyl-1-carboxymethyl]-6-fluoro-7-cyclohexylamino-2,4-(1H, 3H)-guinazolinedione

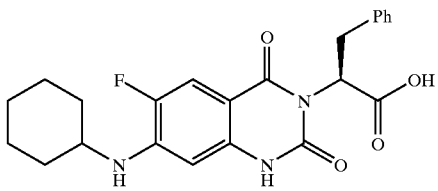

The product was prepared from Fmoc-Phe-Sasrin, methyl 2-(p-nitrophenyl)carbamoyl-4,5-difluorobenzoate, and cyclohexylamine as described above in the General Procedure for Solid Phase Synthesis of 7-Substituted Quinazoline-2,4-diones. $R_t$ 4.1 min. Mass-spectrum (m/z): 426 (M+H)$^+$.

3-[(S)-1-Benzyl-1-carboxymethyl]-6-fluoro-7-(cyclohexylmethyl)-amino-2,4-(1H, 3H)-guinazolinedione

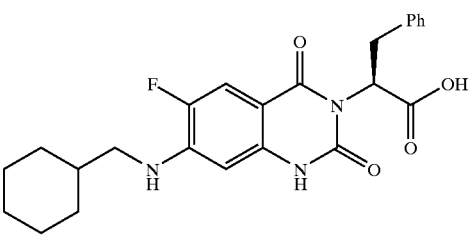

The product was prepared from Fmoc-Phe-Sasrin, methyl 2-(p-nitrophenyl)carbamoyl-4,5-difluorobenzoate, and (cyclohexylmethyl)amine as described above in the General Procedure for Solid Phase Synthesis of 7-Substituted Quinazoline-2,4-diones. $R_t$ 4.4 min. Mass-spectrum (m/z): 440 (M+H)$^+$.

3-[(S)-1-Benzyl-1-carboxymethyl]-6-fluoro-7-benzylamino-2,4-(1H, 3H)-quinazolinedione

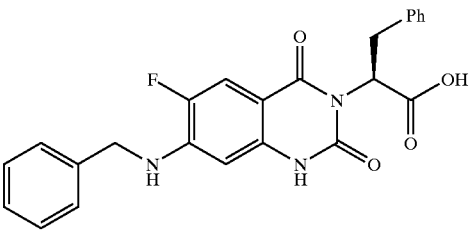

The product was prepared from Fmoc-Phe-Sasrin, methyl 2-(p-nitrophenyl)carbamoyl-4,5-difluorobenzoate, and benzylamine as described above in the General Procedure for Solid Phase Synthesis of 7-Substituted Quinazoline-2,4-diones. $R_t$ 3.8 min. Mass-spectrum (m/z): 434 (M+H)$^+$.

Although the forgoing invention has been described in some detail by way of illustration and example for purposes of clarity and understanding, it will be apparent to those skilled in the art that certain changes and modifications may be practical. Therefore, the description and examples should not be construed as limiting the scope of the invention, which is delineated by the appended claims.

What is claimed is:

1. A combinatorial library comprising compounds of the structure:

P—R—● wherein P is a 2,4-pyrimidinedione selected from the group consisting of a quinazolinedione, a pyrimidopyrimidinedione, a pyridopyrimidinedione, and a pteridinedione; and wherein R is a substituted alkyl chain at the 3-position of the 2,4-pyrimidinedione, ● is a solid support and R—● is selected from the group consisting of:

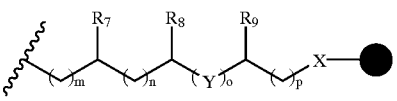

wherein $R_7$, $R_8$ and $R_9$ are independently selected from the group consisting of H, alkyl, aryl, OH, NH$_2$, NHR$_{10}$, $NR_{10}R_{11}$, SH, $SR_{10}$, =O, C(O)R, and an amino acid side chain; and wherein Y is selected from the group consisting of alkyl, aryl, O, NH, and $NR_{10}$; and wherein X is selected from the group consisting of $CO_2$, CO, S, O, NH, $NR_{10}$, C(O)NHO, and C(O)$NR_{10}$; and wherein $R_{10}$ and $R_{11}$ are independently selected from the group consisting of alkyl, aryl and heteroaryl; and further wherein m, n, o, and p vary independently from 0 to 4,

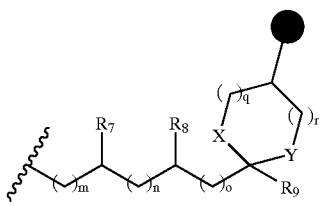

wherein $R_7$, $R_8$ and $R_9$ are independently selected from the group consisting of H, alkyl, aryl, OH, $NH_2$, $NHR_{10}$, $NR_{10}R_{11}$, SH, $SR_{10}$, =O, $C(O)R_{10}$, and an amino acid side chain; and wherein X and Y are independently selected from the group consisting of O and S; and wherein $R_{10}$ and $R_{11}$ are independently selected from the group consisting of alkyl, aryl and heteroaryl; and wherein m, n, and o vary independently from 0 to 4; and wherein q and r vary independently from 0 to 2; and

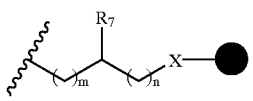

wherein $R_7$ is independently selected from the group consisting of H, alkyl, aryl, OH, $NH_2$, $NHR_{10}$, $NR_{10}R_{11}$, SH, $SR_{10}$, =O, C(O)$R_{11}$, and an amino acid side chain; and wherein X is selected from the group consisting of $CO_2$, CO, S, O, NH, $NR_{10}$, C(O)NHO, and C(O)$NR_{10}$; and wherein $R_{10}$ and $R_{11}$ are independently selected from the group consisting of alkyl, aryl and heteroaryl; and wherein m and n vary independently from 0 to 4.

2. The combinatorial library of claim 1, wherein P is selected from the group consisting of a quinazolinedione, a pyrimidopyrimidinedione, and a pyridopyrimidinedione.

3. The combinatorial library of claim 1, wherein P is a pyridopyrimidinedione.

4. The combinatorial library of claim 1, wherein P is a 2,4-quinazolinedione of the structure:

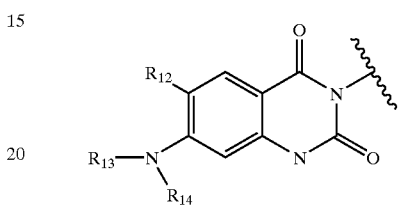

wherein $R_{12}$ is a hydrogen or a halo;
and —$NR_{13}R_{14}$ represents an —$NH_2$,

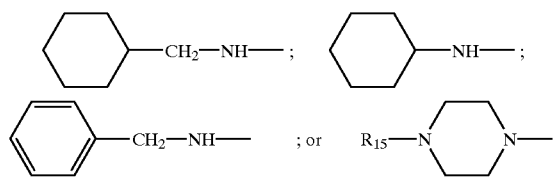

wherein $R_{15}$ is hydrogen or lower alkyl.

5. The combinatorial library of claim 4, wherein $R_{12}$ is fluoro.

* * * * *